US010595530B2

(12) United States Patent
Goodman et al.

(10) Patent No.: US 10,595,530 B2
(45) Date of Patent: *Mar. 24, 2020

(54) COMPOSITIONS AND METHODS FOR THE REMOVAL OF BIOFILMS

(71) Applicants: Nationwide Children's Hospital, Inc., Columbus, OH (US); University of Southern California, Los Angeles, CA (US)

(72) Inventors: Steven D. Goodman, Hilliard, OH (US); Lauren O. Bakaletz, Hilliard, OH (US)

(73) Assignees: Nationwide Children's Hospital, Inc., Columbus, OH (US); University of Southern California, Los Angeles, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/885,800

(22) Filed: Oct. 16, 2015

(65) Prior Publication Data

US 2016/0095316 A1 Apr. 7, 2016

Related U.S. Application Data

(63) Continuation of application No. 13/229,575, filed on Sep. 9, 2011, now abandoned.

(60) Provisional application No. 61/381,377, filed on Sep. 9, 2010.

(51) Int. Cl.
*A01N 37/46* (2006.01)
*A61K 38/17* (2006.01)

(52) U.S. Cl.
CPC .......... *A01N 37/46* (2013.01); *A61K 38/1709* (2013.01); *Y02A 50/401* (2018.01); *Y02A 50/471* (2018.01); *Y02A 50/473* (2018.01); *Y02A 50/481* (2018.01)

(58) Field of Classification Search
None
See application file for complete search history.

(56) References Cited

U.S. PATENT DOCUMENTS

| 6,846,651 | B2 | 1/2005 | Fleischmann et al. |
| 8,933,029 | B2 | 1/2015 | McNicol et al. |
| 8,999,291 | B2* | 4/2015 | Goodman ............ A61K 38/164 424/9.2 |
| 9,017,656 | B2 | 4/2015 | Hancock et al. |
| 9,155,792 | B2 | 10/2015 | Cottarel et al. |
| 9,745,366 | B2 | 8/2017 | Goodman et al. |
| 2002/0132753 | A1 | 9/2002 | Rosen et al. |
| 2003/0060410 | A1* | 3/2003 | Tracey ............... C07K 14/4702 424/85.2 |
| 2003/0099602 | A1 | 5/2003 | Levin et al. |
| 2003/0229065 | A1 | 12/2003 | Levy et al. |
| 2004/0202670 | A1 | 10/2004 | Apicella |
| 2005/0049402 | A1 | 3/2005 | Babcook et al. |
| 2005/0131222 | A1 | 6/2005 | Fleischmann et al. |
| 2005/0221439 | A1 | 10/2005 | Bakaletz et al. |
| 2006/0030539 | A1 | 2/2006 | Nick et al. |
| 2006/0099207 | A1 | 5/2006 | Wu et al. |
| 2006/0121047 | A1 | 6/2006 | Tracey |
| 2006/0228384 | A1 | 10/2006 | Eldridge |
| 2006/0240045 | A1 | 10/2006 | Berthet et al. |
| 2007/0154529 | A1* | 7/2007 | Bullerdiek ............ A61K 8/606 424/445 |
| 2007/0264256 | A1 | 11/2007 | Bakaletz et al. |
| 2009/0029929 | A1 | 1/2009 | Nakajima et al. |
| 2010/0291177 | A1 | 11/2010 | Hermans et al. |
| 2011/0236306 | A1 | 9/2011 | Goodman et al. |
| 2012/0128701 | A1 | 5/2012 | Goodman et al. |
| 2015/0086542 | A1 | 3/2015 | Goodman et al. |
| 2015/0166641 | A1 | 6/2015 | Goodman et al. |
| 2016/0175440 | A1 | 6/2016 | Goodman et al. |

FOREIGN PATENT DOCUMENTS

| JP | 2005-519998 | 7/2005 |
| JP | 2006-506441 | 2/2006 |
| JP | 2006-506467 | 2/2006 |
| JP | 2008-520552 | 6/2008 |
| JP | 2013-529893 | 7/2013 |
| WO | WO-00/47104 A2 | 8/2000 |
| WO | WO-03/026691 A2 | 4/2003 |
| WO | WO-2004/014418 A2 | 2/2004 |
| WO | WO-2004/044001 A2 | 5/2004 |
| WO | WO-2004/072094 A2 | 8/2004 |

(Continued)

OTHER PUBLICATIONS

Singh et al. 2000 (Quorum-sensing signals indicate that cystic fibrosis lungs are infected with bacterial biofilms; Nature 407(12):762-764).*
Whitchurch et al. 2002 (Extracellular DNA Required for Bacterial Biofilm Formation; ; Science 295: 1487).*
Greenspan et al. 1999 (Defining epitopes: It's not as easy as it seems; Nature Biotechnology, 17:936-937).*
Rudikoff et al. 1982 (Single amino acid substitution altering antigen-binding specificity; PNAS, USA, 79(6):1979-1983).*
Bass et al. 2010 (Extracellular DNA: A Major Proinflammatory Component of Pseudomonas aeruginosa Biofilms; The Journal of Immunology 184(11):6386-6395).*
Percival et al. 2015 (Biofilms and Wounds: An Overview of the Evidence; Advances in Wound Care 4(7): 373-381).*

(Continued)

*Primary Examiner* — Mary Maille Lyons
(74) *Attorney, Agent, or Firm* — Foley & Lardner LLP; Antoinette F. Konski

(57) ABSTRACT

Methods of breaking down a biofilm or inhibiting, preventing or treating a microbial infection that produces a biofilm are disclosed, which involves administration of a polypeptide that has one or more HMG-box domains to a subject suffering from the infection or having the biofilm. By competing with microbial proteins that bind to DNA scaffold in the biofilm, these polypeptides destabilize the biofilm leading to destruction and removal of the biofilm by the immune system.

9 Claims, 8 Drawing Sheets
Specification includes a Sequence Listing.

(56) References Cited

FOREIGN PATENT DOCUMENTS

| | | |
|---|---|---|
| WO | WO-2005/025604 A2 | 3/2005 |
| WO | WO-2006/017816 A2 | 2/2006 |
| WO | WO-2006/083301 A2 | 8/2006 |
| WO | WO-2006/114805 A2 | 11/2006 |
| WO | WO-2007/001422 A2 | 1/2007 |
| WO | WO-2011/123396 A1 | 10/2011 |
| WO | WO-2012/034090 | 3/2012 |
| WO | WO-2014/201305 A1 | 12/2014 |

OTHER PUBLICATIONS

Fan et al. 2002 (HMG2 Interacts with the Nucleosome Assembly Protein SET and Is a Target of the Cytotoxic T-Lymphocyte Protease Granzyme A; Molecular and Cellular Biology 22(8): 2810-2820).*
Kirketerp-Moller et al. 2008 (Distribution, Organization, and Ecology of Bacteria in Chronic Wounds; J of Clinical Microbiology 46(8): 2717-2722). (Year: 2008).*
Smith et al. 1996 (Cystic Fibrosis Airway Epithelia Fail to Kill Bacteria because of Abnormal Airway Surface Fluid; Cell 85: 229-236) (Year: 1996).*
Non-Final Office Action in U.S. Appl. No. 14/493,051, dated Apr. 28, 2016.
U.S. Appl. No. 15/078,987, filed Mar. 23, 2016, Research Institute at Nationwide Children's Hospital.
Final Office Action for U.S. Appl. No. 14/535,254, dated Mar. 25, 2016.
Brandstetter, K.A. et al. (2013) "Antibodies Directed Against Integration Host Factor Mediate Biofilm Clearance From Nasopore," The Laryngoscope 123(11):2626-2632.
Brockson, M.E. et al. (2014) "Evaluation of the kinetics and mechanism of action of anti-integration host factor-mediated disruption of bacterial biofilms," Molecular Microbiology 93(6):1246-1258.
Brockson, M.E. et al. (2014) "Evaluation of the kinetics and mechanism of action of anti-integration host factor-mediated disruption of bacterial biofilms," Molecular Microbiology 93(6):1246-1258: Supplementary Material, 6 pages.
Govan, J.R. et al. (1996) "Microbial pathogenesis in cystic fibrosis: mucoid Pseudomonas aeruginosa and Burkholderia cepacia," Microbiol. Rev. 60(3):539-574.
Gustave, J.E. et al. (2013) "Targeting bacterial integration host factor to disrupt biofilms associated with cystic fibrosis," Journal of Cystic Fibrosis 12(4):384-389.
Martinez-Antonio A et al. (2008), "Functional organization of Escherichia coli transcriptional regulatory network", J. Mol. Biol. vol. 381, p. 238-247.
Non-Final Office Action for U.S. Appl. No. 14/493,051, dated Oct. 8, 2015.
Non-Final Office Action for U.S. Appl. No. 14/535,254, dated Sep. 9, 2015.
Novotny, L.A. et al. (2013) "Structural Stability of Burkholderia cenocepacia Biofilms Is Reliant on eDNA Structure and Presence of a Bacterial Nucleic Acid Binding Protein," PLOS One 8(6):e67629, 15 pages.
Restriction Requirement for U.S. Appl. No. 14/535,254, dated Mar. 27, 2015, 8 pages.
Restriction Requirement in U.S. Appl. No. 13/073,782, dated Feb. 20, 2013, 10 pages.
Seikagaku [Biochemistry], 1996, vol. 68, No. 12, pp. 1829-1834.
Whitchurch, C.B. et al. (2002) "Extracellular DNA Required for Bacterial Biofilm Formation," Science 295(5559):1487.
Whitchurch, C.B. et al. (2002) "Extracellular DNA Required for Bacterial Biofilm Formation," Science 295(5559):1487: Supplementary Material, 2 pages.
Adams et al., (2007) "Epitope-mapping the immune response of children with otitis media and adults with chronic obstructive pulmonary disease to the PilA protein of nontypeable Haemophilus influenzae type IV pilus," 107th General Meeting, American Society for Microbiology; 2007; Toronto, ON.
Andersson, U. et al. (2011) "HMGB1 Is a Therapeutic Target for Sterile Inflammation and Infection," Annu. Rev. Immunol. 29:139-162.
Bakaletz et al., (1997) "Relative immunogenicity and efficacy of two synthetic chimeric peptides of fimbrin as vaccinogens against nasopharyngeal colonization by nontypeable Haemophilus influenzae in the chincilla," Vaccine 15(9): 955-961.
Bakaletz et al., (2000) "Epitope mapping of the outer membrane protein P5-Homologous Fimbrin adhesion of nontypeable Haemophilus influenza," Vaccine 68(4):2119-2128.
Bakaletz, L.O. et al. (1999) "Protection against Development of Otitis Media Induced by Nontypeable Haemophilus influenzae by Both Active and Passive Immunization in a Chinchilla Model of Virus-Bacterium Superinfection," Infecion and Immunity 67(6): 2746-2762.
Barve, M.P. et al. (2003) "Cloning and characterization of the mating type (MAT) locus from Ascochyta rabiei (teleomorph: Didymella rabiei) and a MAT phylogeny of legume-associated Ascochyta spp.," Fungal Genetics and Biology 39(2):151-167.
Cho, J.H. et al. (2001) "The modulation of the biological activities of mitochondrial histone Abf2p by yeast PKA and its possible role in the regulation of mitochondrial DNA content during glucose repression," Biochimica et Biophysica Acta 1522(3):175-186.
Cohavy, O. et al. (1999) "Identification of a Novel Mycobacterial Histone H1 Homologue (HupB) as an Antigenic Target of pANCA Monoclonal Antibody and Serum Immunoglobulin A from Patients with Cohn's Disease," Infection and Immunity 67(12):6510-6517.
Estrela, A.B. et al. (2010) "Combining Biofilm-Controlling Compounds and Antibiotics as a Promising New Way to Control Biofilm Infections," Pharmaceuticals 3:1374-1393.
Falciola, L. et al. (1994) "Mutational analysis of the DNA binding domain A of chromosomal protein HMG1," Nucleic Acids Research 22(3):285-292.
Final Office Action in U.S. Appl. No. 13/073,782, dated Mar. 27, 2014, 8 pages.
Final Office Action in U.S. Appl. No. 13/229,575, dated Aug. 29, 2013, 17 pages.
Final Office Action in U.S. Appl. No. 13/229,575, dated Sep. 19, 2014, 34 pages.
Gerstel et al., "Complex Regulation of csgD Promoter Activity by Global Regulatory Proteins," Molecular Microbiology, vol. 49, No. 3, Aug. 2003, pp. 639-654.
Goodman, S.D. et al. (1999) "Replacement of Integration Host Factor Protein-induced DNA Bending by Flexible Regions of DNA," The Journal of Biological Chemistry 274(52):37004-37011.
Goodman, S.D. et al. (2011) "Biofilms can be dispersed by focusing the immune system on a common family of bacterial nucleoid-associated proteins," Mucosal Immunology 4(6):625-637.
Granston, A.E. et al. (1993) "Characterization of a Set of Integration Host Factor Mutants Deficient for DNA Binding," J. Mol. Biol. 234:45-59.
Greenspan, N.S. et al. (1999) "Defining epitopes: It's not as easy as it seems," Nature Biotechnology 17:936-937.
Hall-Stoodley et al., "Evolving concepts in biofilm infections", Cellular Microbiology, vol. 11, No. 7, p. 1034-1043, 2009.
Hall-Stoodley, L. et al. (2008) "Characterization of biofilm matrix, degradation by DNase treatment and evidence of capsule downregulation in Streptococcus pneumoniae clinical isolates," BMC Microbiology 8:173, 16 pages.
Harley, V.R. et al. (2003) "The Molecular Action and Regulation of the Testis-Determining Factors, SRY (Sex-Determining Region on the Y Chromosome) and SOX9 [SRY-Related High-Mobility Group (HMG) Box 9]," Endocrine Reviews 24(4):466-487.
Haruta et al., "A Possible Role of Histone-Like DNA-Binding Protein of Streptococcus intermedius in the Pathogenesis of Bile Duct Damage in Primary Biliary Cirrhosis," Clinical Immunology, vol. 127, No. 2, May 2008, pp. 245-251.
International Search Report for Application No. PCT/US2011/051107, dated Jan. 25, 2012, 5 pages.
Jodar, L. et al. (2002) "Development of vaccines against meningococcal disease," Lancet 359:1499-1508.

(56) References Cited

OTHER PUBLICATIONS

Jurcisek, J.A. et al. (2007) "Biofilms Formed by Nontypeable Haemophilus influenzae In Vivo Contain both Double-Stranded DNA and Type IV Pilin Protein," Journal of Bacteriology 189(10): 3868-3875.
Kamashev, D. et al. (2000) "The histone-like protein HU binds specifically to DNA recombination and repair intermediates," The EMBO Journal 19(23):6527-6535.
Kennedy, B-J. et al. (2000) "Passive Transfer of Antiserum Specific for Immunogens Derived from a Nontypeable Haemophilus influenzae Adhesin and Lipoprotein D Prevents Otitis Media after Heterologous Challenge," Infection and Immunity 68(5):2756-2765.
Kornblit, B. et al. (2007) "The genetic variation of the human HMG1 gene," Tissue Antigens 70:151-156.
Kyd, J.M. et al. (2003) "Efficacy of the 26-Kilodalton Outer Membrane Protein and Two P5 Fimbrin-Derived Immunogens to Induce Clearance of Nontypeable Haemophilus influenzae from the Rat Middle Ear and Lungs as Well as from the Chinchilla Middle Ear and Nasopharynx," Infection and Immunity 71(8):4691-4699.
Labbé, E. et al. (2000) "Association of Smads with lymphoid enhancer binding factor 1/T cell-specific factor mediates cooperative signaling by the transforming growth factor-β and Wnt pathways," Proc. Natl. Acad. Sci. USA 97(15):8358-8363.
Li, L. et al. (2000) "Retroviral cDNA Integration: Stimulation by HMG I Family Proteins," Journal of Virology 74(23):10965-10974.
Meluleni et al., (1995) "Mucoid Pseudomonas aeruginosa Growing in a Biofilm In Vitro Are Killed by Opsonic Antibodies to the Mucoid Exopolysaccharide Capsule but Not by Antibodies Produced During Chronic Lung Infection in Cystic Fibrosis Patients," J. Immunology, 155:2029-2038.
Mouw, K.W. et al. (2007) "Shaping the Borrelia burgdorferi genome: crystal structure and binding properties of the DNA-bending protein Hbb," Molecular Microbiology 63(5):1319-1330.
Murphy, T.F. et al. (2009) "Microbial Interactions in the Respiratory Tract," The Pediatric Infectious Disease Journal 28:S121-S126.
Nakamura, Y. et al. (2001) "HMG Box a in HMG3 Protein Functions as a Mediator of DNA Structural Alteration Together with Box B," J. Biochem. 1129:643-651.
Nash, H.A. et al. (1987) "Overproduction of *Escherichia coli* integration Host Factor, a Protein with Nonidentical Subunits," Journal of Bacteriology 169(9):4124-4127.
NCBI Genebank: P0A6Y1 (Sep. 13, 2005).
Non-Final Office Action for U.S. Appl. No. 14/493,051 dated Mar. 12, 2015.
Non-Final Office Action in U.S. Appl. No. 13/073,782, dated Jun. 10, 2013, 15 pages.
Non-Final Office Action in U.S. Appl. No. 13/073,782, dated Jun. 25, 2014, 5 pages.
Non-Final Office Action in U.S. Appl. No. 13/229,575, dated Jan. 10, 2013, 18 pages.
Non-Final Office Action in U.S. Appl. No. 13/229,575, dated Mar. 31, 2014, 32 pages.
Notice of Allowability for U.S. Appl. No. 13/073,782, dated Mar. 4, 2015, 4 pages.
Notice of Allowance in U.S. Appl. No. 13/073,782, dated Aug. 19, 2014, 11 pages.
Novotny, L.A. et al. (2000) "Epitope mapping of the Outer Membrane Protein P5-Homologous Fimbrin Adhesin of Nontypeable Haemophilus influenzae," Infection and Immunity 68(4):2119-2128.
Novotny, L.A. et al. (2002) "Detection and characterization of pediatric serum antibody to the OMP P5-homologous adhesin of nontypeable Haemophilus influenzae during acute otitis media," Vaccine 20(29-30):3590-3597.
Novotny, L.A. et al. (2003) "The Fourth Surface-Exposed Region of the Outer Membrane Protein P5-Homologous Adhesin of the Nontypable Haemophilus influenzae Is an Immunodominant But Nonprotective Decoying Epitope," The Journal of Immunology 171(4):1978-1983.
Novotny, L.A. et al. (2006) "Passive immunization with human anti-protein D antibodies induced by polysaccharide protein D conjugates protects chinchillas against otitis media after intranasal challenge with Haemophilus influenzae," Vaccine 24(22):4804-4811.
Novotny, L.A. et al. (2010) "Epitope mapping immunodominant regions of the PilA protein of nontypeable Haemophilus influenzae (NTHI) to facilitate the design of two novel chimeric vaccine candidates," Vaccine 28(1):279-289.
Oberto, J. et al. (1994) "Histones, HMG, HU, IHF: Même combat," Biochimie 76:901-908.
Ordway, D.J. et al. (2010) "Evaluation of Standard Chemotherapy in the Guinea Pig Model of Tuberculosis," Antimicrobial Agents and Chemotherapy 54:1820-1833.
Otto, M. (2009) "*Staphylococcus epidermidis*—the 'accidental' pathogen," Nature Reviews Microbiology 7:555-567.
Pedulla, M.L. et al. (1996) "A novel host factor for integration of mycobacteriophage L5," Proc. Natl. Acad. Sci. USA 93:15411-15416.
Prymula, R. et al. (2006) "Pneumococcal capsular polysaccharides conjugated to protein D for prevention of acute otitis media caused by both *Streptococcus pneumoniae* and non-typable Haemophilus influenzae: a randomized double-blind efficacy study," Lancet 367(9512):740-748.
Restriction Requirement for U.S. Appl. No. 14/493,051, dated Nov. 7, 2014, 6 pages.
Restriction Requirement in U.S. Appl. No. 13/229,575, dated Jul. 19, 2012, 9 pages.
Rice, P.A. et al. (1996) "Crystal Structure of an IHF-DNA Complex: A Protein-Induced DNA U-Turn," Cell 87(7):1295-1306.
Sapi, E. et al. (2012) "Characterization of Biofilm Formation by Borrelia burgdorferi In Vitro," PLOS One 7(10):e44277, 1-11.
Schwartz, K. et al. (2012) "Functional Amyloids Composed of Phenol Soluble Modulins Stabilize *Staphylococcus aureus* Biofilms," PLOS Pathogens 8:e1002744, 1-11.
Skolnick, J. et al. (2000) "From genes to protein structure and function: novel applications of computational approaches in the genomic era," Trends in Biotechnology 18:34-39.
Stinson, M.W. et al. (1998) "Streptococcal Histone-Like Protein: Primary Structure of hIpA and Protein Binding to Lipoteichoic Acid and Epithelial Cells," Infection and Immunity 66(1):259-265.
Stoltz, D.A. et al. (2010) "Cystic Fibrosis Pigs Develop Lung Disease and Exhibit Defective Bacterial Eradication at Birth," www.ScienceTranslationMedicine.org 2(29)29ra31:1-8.
Stros, M. et al. (2007) "The HMG-box: a versatile protein domain occurring in a wide variety of DNA-binding proteins," Cell. Mol. Life Sci. 64(19-20):2590-2606.
Swinger et al., (2004) "IHF and HU: flexible architects of bent DNA," Current Opinion in Structural Biology 14 (1): 28-35.
Taudte, S. et al. (2000) "Alanine mutagenesis of high-mobility-group-protein-1 box B (HMG1-B)," Biochem. J. 347:807-814.
Tetz, G.V. et al. (2009) "Effect of DNase and Antibiotics on Biofilm Characteristics," Antimicrobial Agents and Chemotherapy 53(3):1204-1209.
Thomas, J.O. (2001) "HMG1 and 2: architectural DNA-binding proteins," Biochemical Society Transactions 29(Pt 4):395-401.
Winther, B. et al. (2009) "Location of Bacterial Biofilm in the Mucus Overlying the Adenoid by Light Microscopy," Head & Neck Surgery 135(12):1239-1245.
Beech, I.B. et al. (2005) "Microbe-surface interactions in biofouling and biocorrosion processes," International Microbiology 8:157-168.
Catlin, B.W. (1956) "Extracellular Deoxyribonucleic Acid of Bacteria and a Deoxyribonuclease Inhibitor," Science 124:441-442.
Chen, C. et al. (2004) "Substrate specificity of Helicobacter pylori histone-like HU protein is determined by insufficient stabilization of DNA flexure points," Biochem J. 383:343-351.
Collarini, E.J. et al. (2009) "Potent High-Affinity Antibodies for Treatment and Prophylaxis of Respiratory Syncytial Virus Derived from B Cells of Infected Patients," J Immunol 183:6338-6345.
Dalai, B. et al. (2009) "Histone-like protein H-NS regulates biofilm formation and virulence of Actinobacillus pheuropneumonia," Microbial Pathogenesis 46:128-134.

(56) References Cited

OTHER PUBLICATIONS

Eboigbodin, K.E. et al. (2008) "Characterization of the Extracellular Plymeric Substances Produced by *Escherichia coli* Using Infrared Spectroscopic, Proteomic, and Aggregation Studies," Biomacromolecules 9:686-695.

Final Office Action in U.S. Appl. No. 14/493,051, dated Oct. 7, 2016.

Final Office Action in U.S. Appl. No. 15/078,987, dated Dec. 28, 2016.

Garcia-Contreras, R. et al. (2008) "Protein Translation and Cell Death: The Role of Rare tRNAs in Biofilm Formation and in Activating Dormant Phage Killer Genes," PLoS One 3(6):e2394, 1-15.

Goodman, S.D. et al. (1999) "In Vitro Selection of Integration Host Factor Binding Sites," Journal of Bacteriology 181(10):3246-3255.

Hall-Stoodley, L. et al. (2006) "Direct Detection of Bacterial Biofilms on the Middle-Ear Mucosa of Children With Chronic Otitis Media," JAMA 296(2):202-211.

Haluzi, H. et al. (1991) "Genes Coding for Integration Host Factor Are Conserve in Gram-Negative Bacteria," Journal of Bacteriology 173(19):6297-6299.

Haruta, I. et al. (2010) "Long-term bacterial exposure can trigger nonsuppurative destructive cholangitis associated with multifocal epithelial inflammation," Laboratory Investigation 90:577-588.

Hoyle, B. et al. (1991) "Bacterial Resistance to Antibiotics: The Role of Biofilms," Prog. Drug Res. 37:91-105.

Janeway, C.A. et al. (2001) "Manipulating the immune response to fight infection," Immunobiology: The Immune System in Health and Disease, 5th ed.; retrieved online from https://www.ncbi.nlm.nih.gov/books/NBK27131/.

Johnson, R. et al. (2008) "Chapter 8: Bending and Compaction of DNA by Proteins," Protein-Nucleic Acid Interactions: Structural Biology:176-220.

Jurcisek, J. et al. (2005) "Role of Sialic Acid and Complex Carbohydrate Biosynthesis in Biofilm Formation by Nontypeable Haemophilus influenzae in the Chinchilla Middle Ear," Infection and Immunity 73:3210-3218.

Kim, N. et al. (2002) "Proteins Released by Helicobacter pylori In Vitro," Journal of Bacteriology 184(22):6155-6162.

Liu, D. et al. (2008) "The essentiality and involvement of *Streptococcus intermedius* histone-like DNA-binding protein in bacterial viability and normal growth," Molecular Microbiology 68(5):1268-1282.

Lunsford, R.D. et al. (1996) "DNA-Binding Activities in *Streptococcus gordonii*: Indentification of a Receptor-Nickase and a Histone-like Protein," Current Microbiology 32:95-100.

Mukherjee, J. et al. (2011) "Quantitative protein expression and cell surface characteristics of *Escherichia coli* MG1655 biofilms," Proteomics 11:339-351.

Murphy, T.F. et al. (2002) "Biofilm formation by nontypeable Haemophilus influenzae: strain variability, outer membrane antigen expression and role of pili," BMC Microbiology 2:7, 1-8.

Non-Final Office Action in U.S. Appl. No. 14/493,051, dated Jan. 10, 2017.

Non-Final Office Action in U.S. Appl. No. 14/535,254, dated Aug. 12, 2016.

Non-Final Office Action in U.S. Appl. No. 15/078,987, dated Jul. 14, 2016.

Notice of Allowance in U.S. Appl. No. 14/493,051, dated Jan. 27, 2017.

PDB ID: 1IHF: Rice, P.A. et al. (1996), 1 page; retrieved online from http://www.rcsb.org/pdb/explore.do?structureId=IHF.

Petersen, F.C. et al. (2004) "Biofilm Mode of Growth of *Streptococcus intermedius* Favored by a Competence-Stimulating Signaling Peptide," Journal of Bacteriology 186(18):6327-6331.

Pethe, K. et al. (2001) "*Mycobacterium smegmatis* laminin-binding glycoprotein shares epitopes with *Mycobacterium tuberculosis* heparin-binding haemagglutinin," Molecular Microbiology 39(1):89-99.

Segall, A.M. et al. (1994) "Architectural elements in nucleoprotein complexes: interchangeability of specific and non-specific DNA binding proteins," The EMBO Journal 13(19):4536-4548.

Shahrooei, M. et al. "Inhibition of *Staphylococcus epidermidis* Biofilm Formation by Rabbit Polyclonal Antibodies against the SesC Protein," Infection and Immunity 77(9):3670-3678.

Sun, D. et al. (2005) "Inhibition of Biofilm Formation by Monoclonal Antibodies against *Staphylococcus epidermidis* RP62A Accumulation-Associated Protein," Clinical & Diagnostic Laboratory Immunology 12(1):93-100.

Teter, B. et al. (2000) "DNA Bending and Twisting Properties of Integration Host Factor Determined by DNA Cyclization," Plasmid 43:73-84.

Van Schaik, E.J. et al. (2005) "DNA Binding: a Novel Function of Pseudomonas aeruginosa Type IV Pili," Journal of Bacteriology 187(4):1455-1464.

Winters, B.D. et al. (1993) "Isolation and Characterization of a Streptococcus pyogenes Protein that Binds to Basal Laminae of Human Cardiac Muscle," Infection and Immunity 61(8):3259-3264.

Non-Final Office Action in U.S. Appl. No. 14/535,254, dated Jul. 10, 2017.

Non-Final Office Action in U.S. Appl. No. 15/078,987, dated Jun. 14, 2017.

Takeda, T. (2012) "Polyhistidine Affinity Chromatography for Purification and Biochemical Analysis of Fungal Cell Wall-Degrading Enzymes," Affinity Chromatography, Dr. Sameh Magdeldin (Ed.), ISBN: 978-953-51-0325-7, In Tech :177-186.

Non-Final Office Action in U.S. Appl. No. 14/967,228, dated May 19, 2017.

Notice of Allowance in U.S. Appl. No. 14/493,051, dated Apr. 25, 2017.

Final Office Action in U.S. Appl. No. 14/535,254, dated Jun. 9, 2017.

Final Office Action in U.S. Appl. No. 14/967,228, dated Nov. 22, 2017.

George, A.M. et al. (2009) "Cystic fibrosis infections: treatment strategies and prospects," FEMS Microbiol Lett. 300:153-164.

Non-Final Office Action in U.S. Appl. No. 14/535,254, dated Jan. 26, 2018.

Non-Final Office Action in U.S. Appl. No. 15/078,987, dated Mar. 16, 2018.

U.S. Appl. No. 15/999,215, filed Aug. 16, 2018, Goodman et al.

U.S. Appl. No. 16/297,094, filed Mar. 8, 2019, Goodman et al.

U.S. Appl. No. 16/475,654, filed Jul. 2, 2019, Bakaletz et al.

U.S. Appl. No. 16/475,656, Jul. 2, 2019, Bakaletz et al.

U.S. Appl. No. 16/492,582, filed Sep. 9, 2019, Goodman et al.

Andersson et al., "High mobility group 1 protein (HMG-1) stimulates proinflammatory cytokine synthesis in human monocytes", The Journal of Experimental Medicine, vol. 192, No. 4, Aug. 21, 2000, pp. 565-570.

Brady, R.A. et al. (2006) "Identification of *Staphylococcus aureus* Proteins Recognized by the Antibody-Mediated Immune Response to a Biofilm Infection," Infection and Immunity 74(6):3415-3426.

Ceri, H. et al. (1999) "The Calgary Biofilm Device: New Technology for Rapid Determination of Antibiotic Susceptibilities of Bacterial Biofilms," Journal of Clinical Microbiology 37(6):1771-1776.

Coenye, T. et al. (2010) "In vitro and in vivo model systems to study microbial biofilm formation," Journal of Microbiological Methods 83:89-105.

Darouiche, R.O. et al. (2004) "Treatment of Infections Associated with Surgical Implants," N Engl J Med 350:1422-1429.

Devaraj, A. et al., "DNABII proteins play a central role in UPEC biofilm structure", Molecular Microbiology, 2017, 96(6):1119-1135.

Donlan, R.M. et al. (2002) "Biofilms: Survival Mechanisms of Clinically Relevant Microorganisms," Clinical Microbiology Reviews 15(2):167-193.

Durocher, Y. et al. (2002) "High-level and high-throughput recombinant protein production by transient transfection of suspension-growing human 293-EBNA1 cells," Nucleic Acids Research 30(2):e9, 1-9.

(56) References Cited

OTHER PUBLICATIONS

Goldenberg et al., "Genetic and biochemical analysis of IHF/HU hybrid proteins", BioChimie (Paris, FR), vol. 76, No. 10-11, pp. 941-950 (Jan. 1, 1994).

Goshima et al., "Chimeric HU-IHF proteins that alter DNA-binding ability," Gene, vol. 118, No. 1, pp. 97-102 (Sep. 1, 1992).

Hall-Stoodley, L. et al. (2004) "Bacterial Biofilms: From the Natural Environment to Infectious Diseases," Nature Reviews, Microbiology 2:95-108.

Harriman, W.D. et al. (2008) "Antibody discovery via multiplexed single cell characterization," Journal of Immunological Methods 341:135-145.

Harrison, J.J. et al. (2010) "Microtiter susceptibility testing of microbes growing on peg lids: a miniaturized biofilm model for high-throughput screening," Nature Protocols 5(7):1236-1254.

Khrapunov, S. et al. (2006) "Binding then bending: A mechanism for wrapping DNA," PNAS 103(51):19217-19218.

Kristian, S.A. et al. (2003) "Alanylation of Teichoic Acids Protects *Staphylococcus aureus* against Toll-like Receptor 2-Dependent Host Defense in a Mouse Tissue Cage Infection Model," The Journal of Infectoius Diseases 188:414-423.

Liu, D. et al. (2008) "Histone-like DNA binding protein of *Streptococcus intermedius* induces the expression of pro-inflammatory cytokines in human monocytes via activation of ERK1/2 and JNK pathways," Cellular Microbiology 10(1):262-276.

Lutz, H.U. et al. (1990) "Covalent binding of detergent-solubilized membrane glycoproteins to 'Chemobond' plates for ELISA," Journal of Immunological Methods 129:211-220.

Mann, E.E. et al. (2009) "Modulation of eDNA Release and Degradation Affects *Staphylococcus aureus* Biofilm Maturation," PLoS One 4(6):e5822, 1-12.

NCBI Gen Bank Accession No. ACE63256 (Apr. 1, 2009).

NCBI GenBank Accession No. BAA03950 (Feb. 16, 2008).

NCBI GenBank Accession No. CAA47740 (Nov. 11, 1998).

NCBI GenBank Accession No. CAA49169(Feb. 5, 2003).

Swinger, Kerren K. et al., "IHF and HU: flexible architects of bent DNA," Current Opinion in Structural Biology 2004, 14: 28-35.

Zimmerli, W. et al. (1982) "Pathogenesis of Foreign Body Infection: Description and Characteristics of an Animal Model," The Journal of Infectious Diseases 146(4):487-497.

Zimmerli, W. et al. (1984) "Pathogenesis of Foreign Body Infection," J. Clin. Invest. 73:1191-1200.

Zulianello et al., "The HimA and HimD subunits of integration host factor can specifically bind to DNA as homodimers," The EMBO Journal, pp. 1534-1540 (Apr. 1, 1994).

Brown et al., "Tolerance to Single, but Not Multiple, Amino Acid Replacements in Antibody VHCDR2", J Immunol. May 1996, 156(9), pp. 3285-3291.

Non-Final Office Action on U.S. Appl. No. 15/744,713, dated Nov. 8, 2019.

Vajdos et al. "Comprehensive Functional Maps of the Antigen-binding Site of an Anti-ErbB2 Antibody Obtained with Shotgun Scanning Mutagenesis", J Mol. Biol., Jul. 5, 2002, 320(2), pp. 415-428.

\* cited by examiner

Each reaction contained 25 nM *HJ in gel-shift condition

1 & 8. *HJ only
2 & 9. With 25 nM HMGB1
3 & 10. With 50 nM HMGB1
4 & 11. With 100 nM HMGB1
5 & 12. With 200 nM HMGB1
6 & 13. With 400 nM HMGB1
7 & 14. With 500 nM HMGB1

```
                              SEQUENCE LISTING

<160> NUMBER OF SEQ ID NOS: 4

<210> SEQ ID NO 1
<211> LENGTH: 215
<212> TYPE: PRT
<213> ORGANISM: Homo sapiens
<220> FEATURE:
<221> NAME/KEY: misc_feature
<222> LOCATION: (6)..(76)
<223> OTHER INFORMATION: HMGB-UBF_HMG-box
<220> FEATURE:
<221> NAME/KEY: misc_feature
<222> LOCATION: (95)..(143)
<223> OTHER INFORMATION: HMG-box

<400> SEQUENCE: 1

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
                20                  25                  30

Asp Ala Ser Val Asn Phe Ser Glu Phe Ser Lys Lys Cys Ser Glu Arg
            35                  40                  45

Trp Lys Thr Met Ser Ala Lys Glu Lys Gly Lys Phe Glu Asp Met Ala
    50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
                100                 105                 110

Ile Lys Gly Glu His Pro Gly Leu Ser Ile Gly Asp Val Ala Lys Lys
            115                 120                 125

Leu Gly Glu Met Trp Asn Asn Thr Ala Ala Asp Asp Lys Gln Pro Tyr
    130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Glu Glu Glu Glu Asp Glu Glu
                180                 185                 190

Asp Glu Glu Asp Glu Glu Glu Glu Asp Glu Glu Asp Glu Asp Glu
            195                 200                 205

Glu Glu Asp Asp Asp Asp Glu
        210                 215

<210> SEQ ID NO 2
<211> LENGTH: 209
<212> TYPE: PRT
<213> ORGANISM: Homo sapiens
<220> FEATURE:
<221> NAME/KEY: misc_feature
<222> LOCATION: (9)..(76)
<223> OTHER INFORMATION: HMGB-UBF_HMG-box
<220> FEATURE:
<221> NAME/KEY: misc_feature
<222> LOCATION: (95)..(160)
```

<223> OTHER INFORMATION: HMG-box

<400> SEQUENCE: 2

Met Gly Lys Gly Asp Pro Asn Lys Pro Arg Gly Lys Met Ser Ser Tyr
1               5                   10                  15

Ala Phe Phe Val Gln Thr Cys Arg Glu Glu His Lys Lys Lys His Pro
                20                  25                  30

Asp Ser Ser Val Asn Phe Ala Glu Phe Ser Lys Lys Cys Ser Glu Arg
            35                  40                  45

Trp Lys Thr Met Ser Ala Lys Glu Lys Ser Lys Phe Glu Asp Met Ala
    50                  55                  60

Lys Ser Asp Lys Ala Arg Tyr Asp Arg Glu Met Lys Asn Tyr Val Pro
65                  70                  75                  80

Pro Lys Gly Asp Lys Lys Gly Lys Lys Asp Pro Asn Ala Pro Lys
                85                  90                  95

Arg Pro Pro Ser Ala Phe Phe Leu Phe Cys Ser Glu His Arg Pro Lys
                100                 105                 110

Ile Lys Ser Glu His Pro Gly Leu Ser Ile Gly Asp Thr Ala Lys Lys
            115                 120                 125

Leu Gly Glu Met Trp Ser Glu Gln Ser Ala Lys Asp Lys Gln Pro Tyr
    130                 135                 140

Glu Gln Lys Ala Ala Lys Leu Lys Glu Lys Tyr Glu Lys Asp Ile Ala
145                 150                 155                 160

Ala Tyr Arg Ala Lys Gly Lys Ser Glu Ala Gly Lys Lys Gly Pro Gly
                165                 170                 175

Arg Pro Thr Gly Ser Lys Lys Asn Glu Pro Glu Asp Glu Glu Glu
                180                 185                 190

Glu Glu Glu Glu Glu Asp Glu Asp Glu Glu Glu Asp Glu Asp Glu
            195                 200                 205

Glu

<210> SEQ ID NO 3
<211> LENGTH: 200
<212> TYPE: PRT
<213> ORGANISM: Homo sapiens
<220> FEATURE:
<221> NAME/KEY: misc_feature
<222> LOCATION: (9)..(75)
<223> OTHER INFORMATION: HMGB-UBF_HMG-box
<220> FEATURE:
<221> NAME/KEY: misc_feature
<222> LOCATION: (98)..(158)
<223> OTHER INFORMATION: HMGB-UBF_HMG-box

<400> SEQUENCE: 3

Met Ala Lys Gly Asp Pro Lys Lys Pro Lys Gly Lys Met Ser Ala Tyr
1               5                   10                  15

Ala Phe Phe Val Gln Thr Cys Arg Glu Glu His Lys Lys Lys Asn Pro
                20                  25                  30

Glu Val Pro Val Asn Phe Ala Glu Phe Ser Lys Lys Cys Ser Glu Arg
            35                  40                  45

Trp Lys Thr Met Ser Gly Lys Glu Lys Ser Lys Phe Asp Glu Met Ala
    50                  55                  60

Lys Ala Asp Lys Val Arg Tyr Asp Arg Glu Met Lys Asp Tyr Gly Pro
65                  70                  75                  80

Ala Lys Gly Gly Lys Lys Lys Asp Pro Asn Ala Pro Lys Arg Pro
                85                  90                  95

```
Pro Ser Gly Phe Phe Leu Phe Cys Ser Glu Phe Arg Pro Lys Ile Lys
            100                 105                 110

Ser Thr Asn Pro Gly Ile Ser Ile Gly Asp Val Ala Lys Lys Leu Gly
        115                 120                 125

Glu Met Trp Asn Asn Leu Asn Asp Ser Glu Lys Gln Pro Tyr Ile Thr
    130                 135                 140

Lys Ala Ala Lys Leu Lys Glu Lys Tyr Glu Lys Asp Val Ala Asp Tyr
145                 150                 155                 160

Lys Ser Lys Gly Lys Phe Asp Gly Ala Lys Gly Pro Ala Lys Val Ala
                165                 170                 175

Arg Lys Lys Val Glu Glu Glu Asp Glu Glu Glu Glu Glu Glu Glu Glu
                180                 185                 190

Glu Glu Glu Glu Glu Glu Asp Glu
        195                 200

<210> SEQ ID NO 4
<211> LENGTH: 186
<212> TYPE: PRT
<213> ORGANISM: Homo sapiens
<220> FEATURE:
<221> NAME/KEY: misc_feature
<222> LOCATION: (9)..(75)
<223> OTHER INFORMATION: HMG-box
<220> FEATURE:
<221> NAME/KEY: misc_feature
<222> LOCATION: (93)..(158)
<223> OTHER INFORMATION: HMG-box

<400> SEQUENCE: 4

Met Gly Lys Glu Ile Gln Leu Lys Pro Lys Ala Asn Val Ser Ser Tyr
1               5                   10                  15

Val His Phe Leu Leu Asn Tyr Arg Asn Lys Phe Lys Glu Gln Gln Pro
                20                  25                  30

Asn Thr Tyr Val Gly Phe Lys Glu Phe Ser Arg Lys Cys Ser Glu Lys
            35                  40                  45

Trp Arg Ser Ile Ser Lys His Glu Lys Ala Lys Tyr Glu Ala Leu Ala
        50                  55                  60

Lys Leu Asp Lys Ala Arg Tyr Gln Glu Glu Met Met Asn Tyr Val Gly
65                  70                  75                  80

Lys Arg Lys Lys Arg Arg Lys Arg Asp Pro Gln Glu Pro Arg Arg Pro
                85                  90                  95

Pro Ser Ser Phe Leu Leu Phe Cys Gln Asp His Tyr Ala Gln Leu Lys
            100                 105                 110

Arg Glu Asn Pro Asn Trp Ser Val Val Gln Val Ala Lys Ala Thr Gly
        115                 120                 125

Lys Met Trp Ser Thr Ala Thr Asp Leu Glu Lys His Pro Tyr Glu Gln
130                 135                 140

Arg Val Ala Leu Leu Arg Ala Lys Tyr Phe Glu Glu Leu Glu Leu Tyr
145                 150                 155                 160

Arg Lys Gln Cys Asn Ala Arg Lys Lys Tyr Arg Met Ser Ala Arg Asn
                165                 170                 175

Arg Cys Arg Gly Lys Arg Val Arg Gln Ser
                180                 185
```

COMPOSITIONS AND METHODS FOR THE REMOVAL OF BIOFILMS

CROSS REFERENCE TO RELATED APPLICATIONS

This application is a continuation of U.S. patent application Ser. No. 13/229,575, filed Sep. 9, 2011, which claims the benefit under 35 U.S.C. § 119(e) to U.S. Provisional Application No. 61/381,377, filed Sep. 9, 2010, the content of each of which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Oct. 30, 2013, is named 106887-4402_SL.text and is 8,012 bytes in size.

FIELD OF THE INVENTION

This invention generally relates to the methods and compositions to lessen and/or cure clinical or industrial bacterial biofilms.

BACKGROUND

Bacteria persisting in a biofilm in the human body cause about two-thirds of all chronic/recurrent diseases. These biofilms are comprised of bacteria protected by an outer "slime" that is often comprised primarily of DNA which prevents the innate and adaptive immune systems, antibiotics and other antibacterial agents from gaining access to the bacteria inside the biofilm. Biofilms make it extremely difficult to clear the infection from the body. Furthermore, biofilms can act as a reservoir for future acute infections often with lethal consequences.

At least one protein from the DNABII family of proteins is found in all known eubacteria and are naturally found outside of the bacterial cell. While they elicit a strong innate immune response, host subjects fail to naturally produce specific antibody to family members as a result of infection. The major problem with bacterial biofilms is the inability of the host immune system and/or antibiotics and other antimicrobials to gain access to the bacteria protected within the biofilm.

Biofilms are present in an industrial setting as well. For example, biofilms are implicated in a wide range of petroleum process problems, from the production field to the gas station storage tank. In the field, sulfate reducing biofilm bacteria produce hydrogen sulfide (soured oil). In the process pipelines, biofilm activity develops slimes which impede filters and orifices. Biofilm and biofilm organisms also cause corrosion of pipeline and petroleum process equipment. These problems can be manifested throughout an oil or gas production facility to the point where fouling and corrosive biofilm organisms have even been found on the surfaces of final product storage tanks.

In the home, biofilms are found in or on any surface that supports microbial growth, e.g., in drains, on food preparation surfaces, in toilets and in swimming pools and spas.

Biofilms are implicated in a wide range of water processes, both domestic and industrial. They can grow on the surface of process equipment and impede the performance of the equipment, such as degradation of heat transfer or plugging of filters and membranes. Biofilms growing on cooling tower fill can add enough weight to cause collapse of the fill. Biofilms cause corrosion of even highly specialized stainless steels. Biofilms in a water process can degrade the value of a final product. Biofilms growing in drinking water distribution systems can harbor potential pathogenic organisms, corrosive organisms or bacteria that degrade the aesthetic quality of the water.

Thus, a need exists to break through the protective barrier of biofilms to treat or kill the associated bacterial infections and clear them from surfaces and in water systems. This invention satisfies this need and provides related advantages as well.

SUMMARY

It is discovered herein that polypeptides that have one or more HMG-box domains(s), such as HMGB1, can interfere with the structure of extracellular DNA scaffold inside biofilms. By competing with microbial proteins that bind to the DNA scaffold in the biofilm, these polypeptides destabilize the biofilm, leading to destruction and removal of the biofilm by the host immune system.

HMG-box domain(s) enable a protein to bind non-B-type DNA conformations such as kinked or unwound DNA structures. HMG-box domain containing proteins, such as HMGB1, HMGB2, HMGB3 and HMGB4, serve important intracellular functions. HMGB1, for instance, binds to DNA structures that are "pre-bent" and is believed to function in many types of DNA metabolism, e.g., RAG1/2 mediated immunoglobulin recombination. Moreover, HMGB1 proteins are known to be found extracellularly and are released by necrotic but not apoptotic cells as part of the innate immune system. It is observed herein that HMGB1, when added to bacterial biofilm communities, altered DNA based lattice in the biofilms. The altered DNA based lattice can then allow access of the host immune system to the biofilm, permitting the host immune system to clear the biofilm.

The method for using this technology is provided herein. A HMG-box domain containing polypeptide can be used as a therapeutic to destabilize the extracellular DNA shroud of bacterial biofilms. Bacteria that cannot form functional biofilms are more readily cleared by the remainder of the host's immune system.

Accordingly, one embodiment of the present disclosure provides a method for inhibiting, competing or titrating the binding of a DNABII polypeptide or protein to a microbial DNA, comprising contacting the DNABII polypeptide or protein or the microbial DNA with a polypeptide comprising an HMG-box domain, thereby inhibiting, competing or titrating the binding of the DNABII protein or polypeptide to the microbial DNA.

Another embodiment of the present disclosure provides a method for inhibiting, preventing or breaking down a microbial biofilm, comprising contacting the biofilm with a polypeptide comprising an HMG-box domain, thereby inhibiting, preventing or breaking down the microbial biofilm. In some aspects, the contacting is in vitro or in vivo.

Yet another embodiment of the present disclosure provides a method of inhibiting, preventing or breaking down a biofilm in a subject, comprising administering to the subject an effective amount of a polypeptide comprising an HMG-box domain, thereby inhibiting, preventing or breaking down the microbial biofilm.

Also provided, in another embodiment, is a method for inhibiting, preventing or treating a microbial infection that produces a biofilm in a subject, comprising administering to the subject an effective amount of a polypeptide comprising an HMG-box domain, thereby inhibiting, preventing or treating a microbial infection that produces the biofilm in the subject.

In an aspect of any of the above embodiments, the polypeptide comprising an HMG-box domain comprises one or more of:

(a) an isolated or recombinant protein HMGB1 or a fragment thereof that comprises one or more HMG-box domains;

(b) an isolated or recombinant protein HMGB2 or a fragment thereof that comprises one or more HMG-box domains;

(c) an isolated or recombinant protein HMGB3 or a fragment thereof that comprises one or more HMG-box domains;

(d) an isolated or recombinant protein HMGB4 or a fragment thereof that comprises one or more HMG-box domains; or (e) a polypeptide that is at least about 70% identical to any of (a), (b), (c) or (d).

In another aspect, the polypeptide comprising an HMG-box domain comprises an isolated or recombinant protein HMGB1, a polypeptide that is at least about 70% identical to HMGB1 or a fragment thereof that comprises one or more HMG-box domains.

In some aspects, the isolated or recombinant protein is a mammalian protein. In a particular aspect, the mammalian protein is a human protein.

Any of the above method can further comprise administering to the subject an effective amount of one or more of an antimicrobial, an antigenic peptide or an adjuvant. The subject, in one aspect, is a non-human animal or a human patient.

The polypeptide is administered by a method comprising topically, transdermally, sublingually, rectally, vaginally, ocularly, subcutaneous, intramuscularly, intraperitoneally, urethrally, intranasally, by inhalation or orally.

In some aspects, the subject is a pediatric patient and the polypeptide is administered in a formulation for the pediatric patient.

In any of the above embodiments, the biofilm can comprise microbial DNA from a microorganism identified in Table 1.

TABLE 1

Examples of bacterial strains that can generate biofilms

S. sobrinus
S. pyogenes
S. gordonii Challis
S. agalactiae
S. mutans
S. pneumoniae
S. gallolyticus
S. aureus
S. epidermidis
E. coli
H. influenza
Salmonella enteric serovar typhi
Aggregatibacter actinomycetemcomitans
YP_003255304
P. gingivalis
N. gonorrhoeae
N. meningitides
NMB_1302
P. aeruginosa
H. pylori
B. burgdorferi
Moraxella catarrhalis TABLE 1-continued Examples of bacterial strains that can generate biofilms V. cholera El Tor
Burkholderia cenocepacia
Burkholderia pseudomallei
Mycobacterium tuberculosis
Mycobacterium smegmatis
Treponema denticola
Treponema palladium Nichols
Prevotella melaninogenica
Prevotella intermedia
Bordetella pertusis Tohama
Enterococcus faecalis In one embodiment, the polypeptide is administered locally to the microbial infection.

In one embodiment, the present disclosure provides a method for inducing or providing an immune response in a subject in need thereof, comprising administering to the subject an effective amount of a polypeptide comprising an HMG-box domain. In another embodiment, the administration is local to where the immune response is desired.

In one aspect, the polypeptide comprising an HMG-box domain comprises one or more of:

(a) an isolated or recombinant protein HMGB1 or a fragment thereof that comprises one or more HMG-box domains;

(b) an isolated or recombinant protein HMGB2 or a fragment thereof that comprises one or more HMG-box domains;

(c) an isolated or recombinant protein HMGB3 or a fragment thereof that comprises one or more HMG-box domains;

(d) an isolated or recombinant protein HMGB4 or a fragment thereof that comprises one or more HMG-box domains; or (e) a polypeptide that is at least about 70% identical to any of (a), (b), (c) or (d).

In a particular aspect, the polypeptide comprising an HMG-box domain comprises an isolated or recombinant protein HMGB1, a polypeptide that is at least about 70% identical to HMGB1 or a fragment thereof that comprises one or more HMG-box domains.

The isolated or recombinant protein can be a mammalian protein or in a particular aspect, a human protein. The subject, in some aspects, is a non-human animal or a human patient.

Also provided is a kit comprising any one or more agent of the group (a) an isolated or recombinant protein HMGB1 or a fragment thereof that comprises one or more HMG-box domains;

(b) an isolated or recombinant protein HMGB2 or a fragment thereof that comprises one or more HMG-box domains;

(c) an isolated or recombinant protein HMGB3 or a fragment thereof that comprises one or more HMG-box domains;

(d) an isolated or recombinant protein HMGB4 or a fragment thereof that comprises one or more HMG-box domains; or (e) a polypeptide that is at least about 70% identical to any of (a), (b), (c) or (d) and instructions for use in breaking down a biofilm or inhibiting, preventing or treating a microbial infection that produces a biofilm. In one embodiment, the kit further comprises one or more of an adjuvant, an antigenic peptide or an antimicrobial. In yet another embodiment, the kit further comprises a carrier selected from the group of a liquid carrier, a pharmaceutically acceptable carrier, a solid phase carrier, a pharmaceutically acceptable carrier, an implant, a stent, a paste, a gel, a dental implant or a medical implant.

Yet another embodiment of the present disclosure provides use of a polypeptide of the group of:

(a) an isolated or recombinant protein HMGB1 or a fragment thereof that comprises one or more HMG-box domains;

(b) an isolated or recombinant protein HMGB2 or a fragment thereof that comprises one or more HMG-box domains;

(c) an isolated or recombinant protein HMGB3 or a fragment thereof that comprises one or more HMG-box domains;

(d) an isolated or recombinant protein HMGB4 or a fragment thereof that comprises one or more HMG-box domains; or (e) a polypeptide that is at least about 70% identical to any of (a), (b), (c) or (d) in the manufacture of a medicament for breaking down a biofilm or inhibiting, preventing or treating a microbial infection that produces a biofilm.

DETAILED DESCRIPTION

Figure 1:
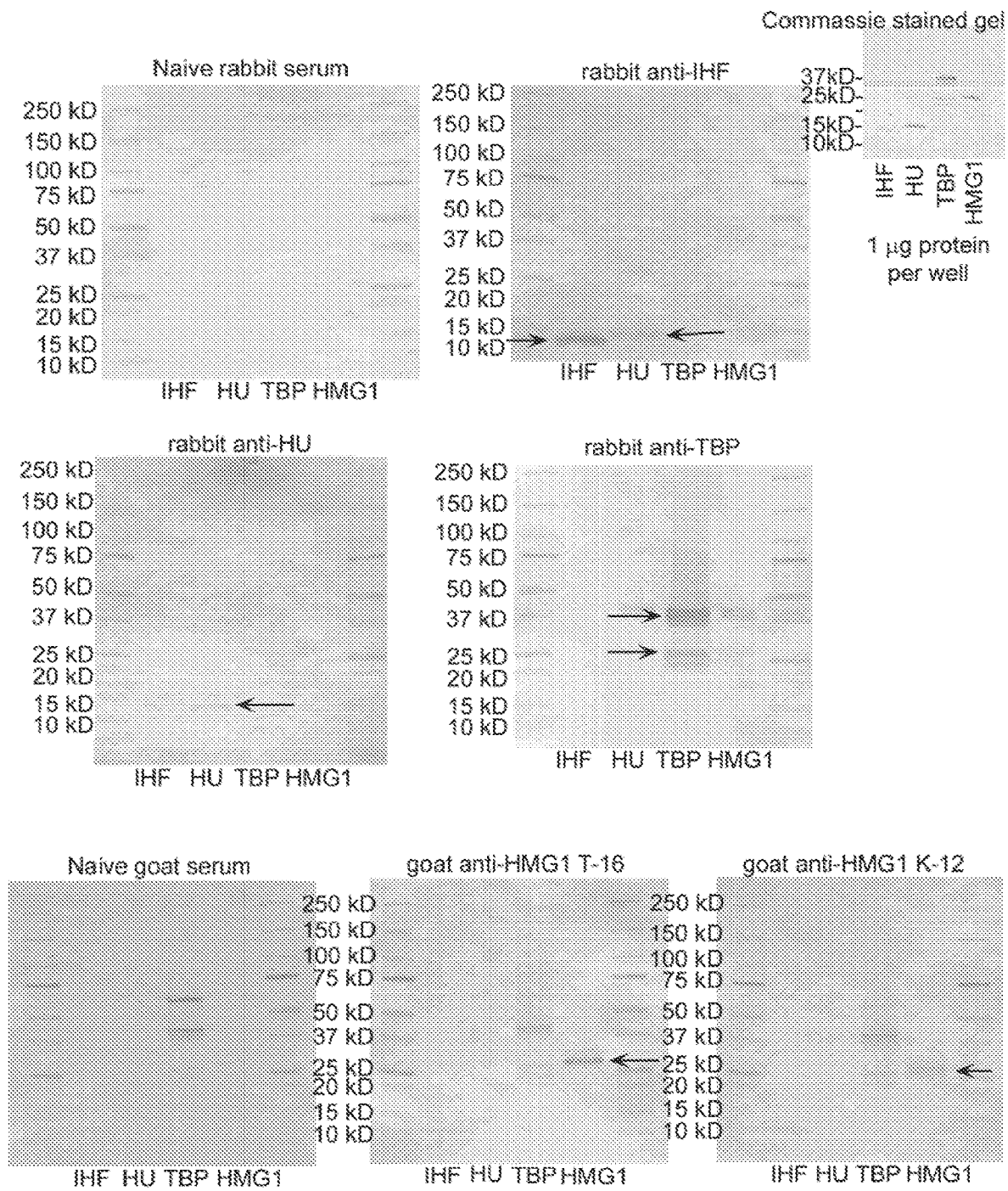
FIG. 1 are Western blot gel pictures each with a different antibody indicating the recognized proteins. Polyclonal antisera to HMGB1 fail to crossreact with DNABII proteins members and polyclonal antisera to DNABII family members fail to crossreact with HMGB1.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices and materials are now described. All technical and patent publications cited herein are incorporated herein by reference in their entirety. Nothing herein is to be construed as an admission that the invention is not entitled to antedate such disclosure by virtue of prior invention.

The practice of the present invention will employ, unless otherwise indicated, conventional techniques of tissue culture, immunology, molecular biology, microbiology, cell biology and recombinant DNA, which are within the skill of the art. See, e.g., Sambrook and Russell eds. (2001) Molecular Cloning: A Laboratory Manual, $3^{rd}$ edition; the series Ausubel et al. eds. (2007) Current Protocols in Molecular Biology; the series Methods in Enzymology (Academic Press, Inc., N.Y.); MacPherson et al. (1991) PCR 1: A Practical Approach (IRL Press at Oxford University Press); MacPherson et al. (1995) PCR 2: A Practical Approach; Harlow and Lane eds. (1999) Antibodies, A Laboratory Manual; Freshney (2005) Culture of Animal Cells: A Manual of Basic Technique, $5^{th}$ edition; Gait ed. (1984) Oligonucleotide Synthesis; U.S. Pat. No. 4,683,195; Hames and Higgins eds. (1984) Nucleic Acid Hybridization; Anderson (1999) Nucleic Acid Hybridization; Hames and Higgins eds. (1984) Transcription and Translation; Immobilized Cells and Enzymes (IRL Press (1986)); Perbal (1984) A Practical Guide to Molecular Cloning; Miller and Calos eds. (1987) Gene Transfer Vectors for Mammalian Cells (Cold Spring Harbor Laboratory); Makrides ed. (2003) Gene Transfer and Expression in Mammalian Cells; Mayer and Walker eds. (1987) Immunochemical Methods in Cell and Molecular Biology (Academic Press, London); and Herzenberg et al. eds (1996) Weir's Handbook of Experimental Immunology.

All numerical designations, e.g., pH, temperature, time, concentration and molecular weight, including ranges, are approximations which are varied (+) or (−) by increments of 1.0 or 0.1, as appropriate, or alternatively by a variation of +/−15%, or alternatively 10%, or alternatively 5% or alternatively 2%. It is to be understood, although not always explicitly stated, that all numerical designations are preceded by the term "about". It also is to be understood, although not always explicitly stated, that the reagents described herein are merely exemplary and that equivalents of such are known in the art.

As used in the specification and claims, the singular form "a", "an" and "the" include plural references unless the context clearly dictates otherwise. For example, the term "a polypeptide" includes a plurality of polypeptides, including mixtures thereof.

As used herein, the term "comprising" is intended to mean that the compositions and methods include the recited elements, but do not exclude others. "Consisting essentially of" when used to define compositions and methods, shall mean excluding other elements of any essential significance to the combination for the intended use. Thus, a composition consisting essentially of the elements as defined herein would not exclude trace contaminants from the isolation and purification method and pharmaceutically acceptable carriers, such as phosphate buffered saline, preservatives and the like. "Consisting of" shall mean excluding more than trace elements of other ingredients and substantial method steps for administering the compositions of this invention. Embodiments defined by each of these transition terms are within the scope of this invention.

A "biofilm" intends a thin layer or an organized community of microorganisms that at times can adhere to the surface of a structure, that may be organic or inorganic, together with the polymers, such as DNA, that they secrete and/or release. The biofilms are very resistant to microbiotics and antimicrobial agents. They live on gingival tissues, teeth and restorations, causing caries and periodontal disease, also known as periodontal plaque disease. They also cause chronic middle ear infections. Biofilms can also form on the surface of dental implants, stents, catheter lines and contact lenses. They grow on pacemakers, heart valve replacements, artificial joints and other surgical implants. The Centers for Disease Control estimate that over 65% of nosocomial (hospital-acquired) infections are caused by biofilms. Fungal biofilms also frequently contaminate medical devices. They cause chronic vaginal infections and lead to life-threatening systemic infections in people with hobbled immune systems. Biofilms also are involved in numerous diseases. For instance, cystic fibrosis patients have *Pseudomonas* infections that often result in antibiotic resistant biofilms.

A "DNABII polypeptide or protein" intends a DNA binding protein or polypeptide that is composed of DNA-binding domains and thus have a specific or general affinity for DNA. In one aspect, they bind DNA in the minor grove. Non-limiting examples of DNABII proteins are an integration host factor (IHF) protein and a histone-like protein from *E. coli* strain U93 (HU). Other DNA binding proteins that can be associated with the biofilm include DPS (Genbank Accession No.: CAA49169), H-NS (Genbank Accession No.: CAA47740), Hfq (Genbank Accession No.: ACE63256), CbpA (Genbank Accession No.: BAA03950) and CbpB (Genbank Accession No.: NP_418813).

An "integration host factor" or "IHF" protein is a bacterial protein that is used by bacteriophages to incorporate their DNA into the host bacteria. These are DNA binding proteins that function in genetic recombination as well as in transcription and translational regulation. They also bind extracellular microbial DNA. The genes that encode the IHF protein subunits in *E. coli* are himA (Genbank accession No.: POA6X7.1) and himD (POA6Y1.1) genes. Homologs for these genes are found in other organisms, and peptides corresponding to these genes from other organisms can be found in Table 1.

"HMGB1" is a high mobility group box (HMGB) 1 protein that is reported to bind to and distort the minor groove of DNA and is an example of an interfering agent.

Recombinant or isolated protein and polypeptide are commercially available from Atgenglobal, ProSpecBio, Protein1 and Abnova.

"HU" or "histone-like protein from *E. coli* strain U93" refers to a class of heterodimeric proteins typically associated with *E. coli*. HU proteins are known to bind DNA junctions. Related proteins have been isolated from other microorganisms. The complete amino acid sequence of *E. coli* HU was reported by Laine et al. (1980) Eur. J. Biochem. 103(3):447-481. Antibodies to the HU protein are commercially available from Abcam.

"Microbial DNA" intends single or double stranded DNA from a microorganism that produces a biofilm.

"Inhibiting, preventing or breaking down" a biofilm intends the prophylactic or therapeutic reduction in the structure of a biofilm. In one aspect, the terms "inhibiting, competing or titrating" intend a reduction in the formation of the DNA/protein matrix (for example as shown in FIG. 1) that is a component of a microbial biofilm.

A "bent polynucleotide" intends a double strand polynucleotide that contains a small loop on one strand which does not pair with the other strand and any polynucleotide where the end to end distance is reduced beyond natural thermal fluctuations i.e. that is bending beyond the persistence length of 150 bp for native B-form double stranded DNA. In some embodiments, the loop is from 1 base to about 20 bases long, or alternatively from 2 bases to about 15 bases long, or alternatively from about 3 bases to about 12 bases long, or alternatively from about 4 bases to about 10 bases long, or alternatively has about 4, 5, or 6, or 7, or 8, or 9 or 10 bases.

A "subject" of diagnosis or treatment is a cell or an animal such as a mammal or a human. Non-human animals subject to diagnosis or treatment and are those subject to infections or animal models, for example, simians, murines, such as, rats, mice, chinchilla, canine, such as dogs, leporids, such as rabbits, livestock, sport animals and pets.

The term "protein", "peptide" and "polypeptide" are used interchangeably and in their broadest sense refer to a compound of two or more subunit amino acids, amino acid analogs or peptidomimetics. The subunits may be linked by peptide bonds. In another embodiment, the subunit may be linked by other bonds, e.g., ester, ether, etc. A protein or peptide must contain at least two amino acids and no limitation is placed on the maximum number of amino acids which may comprise a protein's or peptide's sequence. As used herein the term "amino acid" refers to either natural and/or unnatural or synthetic amino acids, including glycine and both the D and L optical isomers, amino acid analogs and peptidomimetics.

The term "isolated" or "recombinant" as used herein with respect to nucleic acids, such as DNA or RNA, refers to molecules separated from other DNAs or RNAs, respectively that are present in the natural source of the macromolecule as well as polypeptides. The term "isolated or recombinant nucleic acid" is meant to include nucleic acid fragments which are not naturally occurring as fragments and would not be found in the natural state. The term "isolated" is also used herein to refer to polynucleotides, polypeptides and proteins that are isolated from other cellular proteins and is meant to encompass both purified and recombinant polypeptides. In other embodiments, the term "isolated or recombinant" means separated from constituents, cellular and otherwise, in which the cell, tissue, polynucleotide, peptide, polypeptide, protein, antibody or fragment(s) thereof, which are normally associated in nature. For example, an isolated cell is a cell that is separated from tissue or cells of dissimilar phenotype or genotype. An isolated polynucleotide is separated from the 3' and 5' contiguous nucleotides with which it is normally associated in its native or natural environment, e.g., on the chromosome. As is apparent to those of skill in the art, a non-naturally occurring polynucleotide, peptide, polypeptide, protein, antibody or fragment(s) thereof, does not require "isolation" to distinguish it from its naturally occurring counterpart.

It is to be inferred without explicit recitation and unless otherwise intended, that when the present invention relates to a polypeptide, protein, polynucleotide or antibody, an equivalent or a biologically equivalent of such is intended within the scope of this invention. As used herein, the term "biological equivalent thereof" is intended to be synonymous with "equivalent thereof" when referring to a reference protein, antibody, polypeptide or nucleic acid, intends those having minimal homology while still maintaining desired structure or functionality. Unless specifically recited herein, it is contemplated that any polynucleotide, polypeptide or protein mentioned herein also includes equivalents thereof. For example, an equivalent intends at least about 70% homology or identity, or alternatively about 80% homology or identity and alternatively, at least about 85%, or alternatively at least about 90%, or alternatively at least about 95% or alternatively 98% percent homology or identity and exhibits substantially equivalent biological activity to the reference protein, polypeptide or nucleic acid. In another aspect, the term intends a polynucleotide that hybridizes under conditions of high stringency to the reference polynucleotide or its complement.

A polynucleotide or polynucleotide region (or a polypeptide or polypeptide region) having a certain percentage (for example, 80%, 85%, 90% or 95%) of "sequence identity" to another sequence means that, when aligned, that percentage of bases (or amino acids) are the same in comparing the two sequences. The alignment and the percent homology or sequence identity can be determined using software programs known in the art, for example those described in Current Protocols in Molecular Biology (Ausubel et al., eds. 1987) Supplement 30, section 7.7.18, Table 7.7.1. Preferably, default parameters are used for alignment. A preferred alignment program is BLAST, using default parameters. In particular, preferred programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: ncbi.nlm.nih.gov/cgi-bin/BLAST.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 30% identity or alternatively less than 25% identity, less than 20% identity, or alternatively less than 10% identity with one of the sequences of the present invention.

"Homology" or "identity" or "similarity" can also refer to two nucleic acid molecules that hybridize under stringent conditions to the reference polynucleotide or its complement.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

Examples of stringent hybridization conditions include: incubation temperatures of about 25° C. to about 37° C.; hybridization buffer concentrations of about 6×SSC to about 10×SSC; formamide concentrations of about 0% to about 25%; and wash solutions from about 4×SSC to about 8×SSC. Examples of moderate hybridization conditions include: incubation temperatures of about 40° C. to about 50° C.; buffer concentrations of about 9×SSC to about 2×SSC; formamide concentrations of about 30% to about 50%; and wash solutions of about 5×SSC to about 2×SSC. Examples of high stringency conditions include: incubation temperatures of about 55° C. to about 68° C.; buffer concentrations of about 1×SSC to about 0.1×SSC; formamide concentrations of about 55% to about 75%; and wash solutions of about 1×SSC, 0.1×SSC, or deionized water. In general, hybridization incubation times are from 5 minutes to 24 hours, with 1, 2, or more washing steps, and wash incubation times are about 1, 2, or 15 minutes. SSC is 0.15 M NaCl and 15 mM citrate buffer. It is understood that equivalents of SSC using other buffer systems can be employed.

As used herein, the terms "treating," "treatment" and the like are used herein to mean obtaining a desired pharmacologic and/or physiologic effect. The effect may be prophylactic in terms of completely or partially preventing a disorder or sign or symptom thereof and/or may be therapeutic in terms of a partial or complete cure for a disorder and/or adverse effect attributable to the disorder.

To "prevent" intends to prevent a disorder or effect in vitro or in vivo in a system or subject that is predisposed to the disorder or effect. An example of such is preventing the formation of a biofilm in a system that is infected with a microorganism known to produce one.

"Pharmaceutically acceptable carriers" refers to any diluents, excipients or carriers that may be used in the compositions of the invention. Pharmaceutically acceptable carriers include ion exchangers, alumina, aluminum stearate, lecithin, serum proteins, such as human serum albumin, buffer substances, such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Suitable pharmaceutical carriers are described in Remington's Pharmaceutical Sciences, Mack Publishing Company, a standard reference text in this field. They are preferably selected with respect to the intended form of administration, that is, oral tablets, capsules, elixirs, syrups and the like and consistent with conventional pharmaceutical practices.

"Administration" can be effected in one dose, continuously or intermittently throughout the course of treatment. Methods of determining the most effective means and dosage of administration are known to those of skill in the art and will vary with the composition used for therapy, the purpose of the therapy, the target cell being treated and the subject being treated. Single or multiple administrations can be carried out with the dose level and pattern being selected by the treating physician. Suitable dosage formulations and methods of administering the agents are known in the art. Route of administration can also be determined and method of determining the most effective route of administration are known to those of skill in the art and will vary with the composition used for treatment, the purpose of the treatment, the health condition or disease stage of the subject being treated and target cell or tissue. Non-limiting examples of route of administration include oral administration, nasal administration, injection and topical application.

The term "effective amount" refers to a quantity sufficient to achieve a beneficial or desired result or effect. In the context of therapeutic or prophylactic applications, the effective amount will depend on the type and severity of the condition at issue and the characteristics of the individual subject, such as general health, age, sex, body weight, and tolerance to pharmaceutical compositions. In the context of an immunogenic composition, in some embodiments the effective amount is the amount sufficient to result in a protective response against a pathogen. In other embodiments, the effective amount of an immunogenic composition is the amount sufficient to result in antibody generation against the antigen. In some embodiments, the effective amount is the amount required to confer passive immunity on a subject in need thereof. With respect to immunogenic compositions, in some embodiments the effective amount will depend on the intended use, the degree of immunogenicity of a particular antigenic compound, and the health/responsiveness of the subject's immune system, in addition to the factors described above. The skilled artisan will be able to determine appropriate amounts depending on these and other factors.

In the case of an in vitro application, in some embodiments the effective amount will depend on the size and nature of the application in question. It will also depend on the nature and sensitivity of the in vitro target and the methods in use. The skilled artisan will be able to determine the effective amount based on these and other considerations. The effective amount may comprise one or more administrations of a composition depending on the embodiment.

The agents and compositions can be used in the manufacture of medicaments and for the treatment of humans and other animals by administration in accordance with conventional procedures, such as an active ingredient in pharmaceutical compositions.

An agent of the present invention can be administered for therapy by any suitable route of administration. It will also be appreciated that the preferred route will vary with the condition and age of the recipient and the disease being treated.

An example of a solid phase support include glass, polystyrene, polypropylene, polyethylene, dextran, nylon, amylases, natural and modified celluloses, polyacrylamides, gabbros and magnetite. The nature of the carrier can be either soluble to some extent or insoluble. The support material may have virtually any possible structural configuration so long as the coupled molecule is capable of binding to a polynucleotide, polypeptide or antibody. Thus, the support configuration may be spherical, as in a bead or cylindrical, as in the inside surface of a test tube or the external surface of a rod. Alternatively, the surface may be flat such as a sheet, test strip, etc. or alternatively polystyrene beads. Those skilled in the art will know many other suitable carriers for binding antibody or antigen or will be able to ascertain the same by use of routine experimentation.

As used herein, an "antibody" includes whole antibodies and any antigen binding fragment or a single chain thereof. Thus the term "antibody" includes any protein or peptide containing molecule that comprises at least a portion of an immunoglobulin molecule. Examples of such include, but are not limited to a complementarity determining region (CDR) of a heavy or light chain or a ligand binding portion thereof, a heavy chain or light chain variable region, a heavy chain or light chain constant region, a framework (FR) region or any portion thereof or at least one portion of a binding protein.

The antibodies can be polyclonal or monoclonal and can be isolated from any suitable biological source, e.g., murine, rat, sheep or canine.

"Immune response" broadly refers to the antigen-specific responses of lymphocytes to foreign substances. Any substance that can elicit an immune response is said to be "immunogenic" and is referred to as an "immunogen". All immunogens are antigens, however, not all antigens are immunogenic. An immune response of this invention can be humoral (via antibody activity) or cell-mediated (via T cell activation).

As used herein, the term "inducing an immune response in a subject" is a term well understood in the art and intends that an increase of at least about 2-fold, more preferably at least about 5-fold, more preferably at least about 10-fold, more preferably at least about 100-fold, even more preferably at least about 500-fold, even more preferably at least about 1000-fold or more in an immune response to an antigen (or epitope) can be detected or measured, after introducing the antigen (or epitope) into the subject, relative to the immune response (if any) before introduction of the antigen (or epitope) into the subject. An immune response to an antigen (or epitope), includes, but is not limited to, production of an antigen-specific (or epitope-specific) antibody and production of an immune cell expressing on its surface a molecule which specifically binds to an antigen (or epitope). Methods of determining whether an immune response to a given antigen (or epitope) has been induced are well known in the art. For example, antigen-specific antibody can be detected using any of a variety of immunoassays known in the art, including, but not limited to, ELISA, wherein, for example, binding of an antibody in a sample to an immobilized antigen (or epitope) is detected with a detectably-labeled second antibody (e.g., enzyme-labeled mouse anti-human Ig antibody).

The term "modulate an immune response" includes inducing (increasing, eliciting) an immune response; and reducing (suppressing) an immune response. An immunomodulatory method (or protocol) is one that modulates an immune response in a subject.

Polypeptides

An "HMG domain" or "high mobility group (HMG) box domain" refers to an amino acid sequence that is involved in binding DNA (Stros et al., Cell Mol Life Sci. 64(19-20): 2590-606 (2007)). In one embodiment, the structure of the HMG-box domain consists of three helices in an irregular array. In another embodiment, an HMG-box domain enables a protein to bind non-B-type DNA conformations (kinked or unwound) with high affinity. HMG-box domains can be found in high mobility group proteins, which are involved in the regulation of DNA-dependent processes such as transcription, replication and DNA repair, all of which require changing the conformation of chromatin (Thomas (2001) Biochem. Soc. Trans. 29(Pt 4):395-401).

A "polypeptide comprising an HMG-box domain" or alternatively an "HMG-box protein", refers to a polypeptide or protein that contains one or more HMG-box domains. Identification of an HMG-box domain can be carried by the BLAST™ program or comparing a sequence with known HMG-box domain sequences. HMG-box proteins are found in a variety of eukaryotic organisms and can be broadly divided into two groups, based on sequence-dependent and sequence-independent DNA recognition; the former usually contain one HMG-box motif, while the latter can contain multiple HMG-box motifs. Non-limiting examples of polypeptides comprising an HMG-box domain include HMG1 (HMGB1), HMG2(HMGB2), HMGB3 and HMGB4 non-histone components of chromatin; SRY (sex determining region Y protein) involved in differential gonadogenesis; the SOX family of transcription factors (Harley et al. (2003) Endocr. Rev. 24(4):466-87); sequence-specific LEFT (lymphoid enhancer binding factor 1) and TCF-1 (T-cell factor 1) involved in regulation of organogenesis and thymocyte differentiation (Labbé et al. (2000) Proc. Natl. Acad. Sci. USA. 97(15):8358-63); structure-specific recognition protein SSRP involved in transcription and replication; MTF1 mitochondrial transcription factor; nucleolar transcription factors UBF 1/2 (upstream binding factor) involved in transcription by RNA polymerase I; Abf2 yeast ARS-binding factor (Cho et al. (2001) Biochim. Biophys. Acta. 1522(3):175-86); yeast transcription factors Ixr1, Rox1, Nhp6b and Spp41; mating type proteins (MAT) involved in the sexual reproduction of fungi (Barve et al. (2003) Fungal Genet. Biol. 39(2):151-67); and the YABBY plant-specific transcription factors.

Exemplary sequences of polypeptides comprising an HMG-box domain include NP_002119 (human HMGB1) (SEQ ID NO: 1), NP_001124160 (human HMGB2) (SEQ ID NO: 2), NP_005333 (human HMGB3) (SEQ ID NO: 3) and NP_660206 (human HMGB4) (SEQ ID NO: 4). Amino acid residues from about 9 to about 76 of the human HMGB1, for example, form an HMG-box domain and amino acid residues from about 90 to about 138 form another HMG-box domain. An HMGB1 fragment that contains either of these two HMG-box domains, for example, also constitutes a polypeptide comprising an HMG-box domain, within the meaning of the present disclosure.

Accordingly, a polypeptide comprising an HMG-box domain, as contemplated in the present disclosure, intends any of the above described proteins, fragments of these proteins that contain one or more of the HMG-box domain or equivalents of these proteins or fragments. As used herein, an equivalent of a polypeptide refers to a sequence that is at least about 70%, or alternatively at least about 75%, or at least about 80%, or at least about 85%, or at least about 90%, or at least about 95%, or at least about 98% or at least about 99% identical to the reference polypeptide. In some aspects, the equivalent of a polypeptide retains the intended function and/or structural characteristics of the polypeptide, e.g., containing an HMG-box domain. In one aspect, the equivalent polypeptide includes a domain that is at least about 70%, or alternatively at least about 80%, or at least about 85%, or at least about 90%, or at least about 95%, or at least about 98% or at least about 99% identical to the HMG-box domain. In some aspects, such an equivalent domain retains the function and/or structural characteristics of the HMB-box domain, e.g., binding to a HMB-box binding target. In one aspect, the equivalent polypeptide can hybridize with the polypeptide under stringent conditions.

The polypeptides comprising an HMG-box domain are intended to include wildtype and recombinantly produced polypeptides and proteins from prokaryotic and eukaryotic host cells, as well as muteins, analogs and fragments thereof. In some embodiments, the term also includes antibodies and anti-idiotypic antibodies. Such polypeptides can be isolated or produced using the methods identified below.

The proteins and polypeptides are obtainable by a number of processes known to those of skill in the art, which include purification, chemical synthesis and recombinant methods. Polypeptides can be isolated from preparations such as host cell systems. by methods such as immunoprecipitation with antibody and standard techniques such as gel filtration, ion-exchange, reversed-phase and affinity chromatography. For such methodology, see for example Deutscher et al. (1999) Guide To Protein Purification: Methods In Enzymology (Vol. 182, Academic Press). Accordingly, this invention also provides the processes for obtaining these polypeptides as well as the products obtainable and obtained by these processes.

The polypeptides also can be obtained by chemical synthesis using a commercially available automated peptide synthesizer such as those manufactured by Perkin/Elmer/Applied Biosystems, Inc., Model 430A or 431A, Foster City, Calif., USA. The synthesized polypeptide can be precipitated and further purified, for example by high performance liquid chromatography (HPLC). Accordingly, this invention also provides a process for chemically synthesizing the proteins of this invention by providing the sequence of the protein and reagents, such as amino acids and enzymes and linking together the amino acids in the proper orientation and linear sequence.

Alternatively, the proteins and polypeptides can be obtained by well-known recombinant methods as described, for example, in Sambrook et al. (1989) supra, using the host cell and vector systems described herein.

The polypeptides of this invention also can be combined with various solid phase carriers, such as an implant, a stent, a paste, a gel, a dental implant or a medical implant or liquid phase carriers, such as beads, sterile or aqueous solutions, pharmaceutically acceptable carriers, suspensions or emulsions. Examples of non-aqueous solvents include propyl ethylene glycol, polyethylene glycol and vegetable oils. When used to prepare antibodies or induce an immune response in vivo, the carriers also can include an adjuvant that is useful to non-specifically augment a specific immune response. A skilled artisan can easily determine whether an adjuvant is required and select one. However, for the purpose of illustration only, suitable adjuvants include, but are not limited to Freund's Complete and Incomplete, mineral salts and polynucleotides. Other suitable adjuvants include monophosphoryl lipid A (MPL), mutant derivatives of the heat labile enterotoxin of *E. coli*, mutant derivatives of cholera toxin, CPG oligonucleotides and adjuvants derived from squalene.

Therapeutic Methods

One embodiment of the present disclosure provides a method for inhibiting, competing or titrating the binding of a DNABII polypeptide or protein to a microbial DNA, comprising contacting the DNABII polypeptide or protein or the microbial DNA with a polypeptide comprising an HMG-box domain, thereby inhibiting, competing or titrating the binding of the DNABII protein or polypeptide to the microbial DNA.

Polypeptides having one or more HMG-box domains are known in the art and further described above. One such example is HMGB1 from eukaryotes, a non-specific DNA binding protein. It was known that HMGB1 is released from cells during necrosis, but not apoptosis, and is also released by macrophage stimulated with endotoxin and proinflammatory cytokines Released HMGB1 recruits neutrophils and act as a cytokine to promote inflammation. HMGB1 aksi activates dendritic cells and promotes their functional maturation and response to lymph node chemokines.

HMGB1 binds in the minor groove of DNA, but is not homologous to DNABII family proteins. The data presented in Example 2, however, shows that HMGB1 has a high affinity for bent DNA structures and is functionally similar to DNABII.

Another embodiment of the present disclosure provides a method for inhibiting, preventing or breaking down a microbial biofilm, comprising contacting the biofilm with a polypeptide comprising an HMG-box domain, thereby inhibiting, preventing or breaking down the microbial biofilm. In some aspects, the contacting is in vitro or in vivo.

Yet another embodiment of the present disclosure provides a method of inhibiting, preventing or breaking down a biofilm in a subject, comprising administering to the subject an effective amount of a polypeptide comprising an HMG-box domain, thereby inhibiting, preventing or breaking down the microbial biofilm.

Also provided, in another embodiment, is a method for inhibiting, preventing or treating a microbial infection that produces a biofilm in a subject, comprising administering to the subject an effective amount of a polypeptide comprising an HMG-box domain, thereby inhibiting, preventing or treating a microbial infection that produces the biofilm in the subject.

In an aspect of any of the above embodiments, the polypeptide comprising, or alternatively consisting essentially of, or yet further consisting of an HMG-box domain that also comprises or alternatively consisting essentially of, or yet further consisting of one or more of:

(a) an isolated or recombinant protein HMGB1 or a fragment thereof that comprises or alternatively consists essentially of, or yet further consists of one or more HMG-box domains;

(b) an isolated or recombinant protein HMGB2 or a fragment thereof that comprises or alternatively consists essentially of, or yet further consists of one or more HMG-box domains;

(c) an isolated or recombinant protein HMGB3 or a fragment thereof that comprises or alternatively consists essentially of, or yet further consists of one or more HMG-box domains;

(d) an isolated or recombinant protein HMGB4 or a fragment thereof that comprises or alternatively consists essentially of, or yet further consists of one or more HMG-box domains; or (e) a polypeptide that is at least about 70%, or alternatively at least about 75%, or at least about 80%, or at least about 85%, or at least about 90%, or at least about 95%, or at least about 98% or at least about 99% identical to any of (a), (b), (c) or (d).

In another aspect, the polypeptide comprising an HMG-box domain comprises or alternatively consists essentially of, or yet further consists of an isolated or recombinant protein HMGB1, a polypeptide that is at least about 70%, or at least about 75%, or at least about 80%, or at least about 85%, or at least about 90%, or at least about 95%, or at least about 98% or at least about 99% identical to HMGB1, or a fragment thereof that comprises or alternatively consists essentially of, or yet further consists of one or more HMG-box domains.

In some aspect, the polypeptide comprising an HMG-box domain comprises or alternatively consists essentially of, or yet further consists of a biological equivalent to any polypeptide recited above.

In some aspects, the isolated or recombinant protein is a mammalian protein. In a particular aspect, the mammalian protein is a human protein.

Any of the above method can further comprise or alternatively consists essentially of, or yet further consists of administering to the subject an effective amount of one or more of an antimicrobial, an antigenic peptide or an adjuvant. The subject, in one aspect, is a non-human animal or a human patient.

The polypeptide is administered by a method comprising topically, transdermally, sublingually, rectally, vaginally, ocularly, subcutaneous, intramuscularly, intraperitoneally, urethrally, intranasally, by inhalation or orally.

In some aspects, the subject is a pediatric patient and the polypeptide is administered in a formulation for the pediatric patient.

In any of the above embodiments, the biofilm can comprise microbial DNA from a microorganism identified in Table 1.

In one embodiment, the polypeptide is administered locally to the microbial infection.

In one embodiment, the present disclosure provides a method for inducing or providing an immune response in a subject in need thereof, comprising or alternatively consisting essentially of, or yet further consisting of administering to the subject an effective amount of a polypeptide comprising an HMG-box domain. In another embodiment, the administration is local to where the immune response is desired. Examples of polypeptides comprising an HMG-box domain are described above.

The isolated or recombinant protein can be a mammalian protein or in a particular aspect, a human protein. The subject, in some aspects, is a non-human animal or a human patient.

The agents and compositions of this invention can be concurrently or sequentially administered with other antimicrobial agents and/or surface antigens. In one particular aspect, administration is locally to the site of the infection. Other non-limiting examples of administration include by one or more method comprising transdermally, sublingually, rectally, vaginally, ocularly, subcutaneous, intramuscularly, intraperitoneally, intranasally, by inhalation or orally.

Also provided, in one embodiment, is use of any of the above described polypeptide comprising or alternatively consisting essentially of, or yet further consisting of an HMG-box domain for the manufacture of a medicament in breaking down a biofilm or inhibiting, preventing or treating a microbial infection that produces a biofilm.

For some of these methods the contacting can be performed in vitro or in vivo. When the contacting is in vitro, the method provides a means to determine efficacy of the agents of this invention prior to animal or clinical studies and can be used to determine if the agents of this invention work synergistically with additional antimicrobials. When performed in vivo in an animal model, the method provides a means to determine efficacy of the agents of this invention prior to studies in human patients and can be used to determine if the agents of this invention work synergistically with additional antimicrobials.

Microbial infections and disease that can be treated by the methods of this invention include infection by the organisms identified in Table 1, e.g., *Streptococcus agalactiae, Neisseria meningitidis, Treponemes, denticola, pallidum, Burkholderia cepacia* or *Burkholderia pseudomallei*. In one aspect, the microbial infection is one or more of *Haemophilus influenzae* (nontypeable), *Moraxella catarrhalis, Streptococcus pneumoniae, Streptococcus pyogenes, Pseudomonas aeruginosa, Mycobacterium tuberculosis*. These microbial infections may be present in the upper, mid or lower airway (otitis, sinusitis or bronchitis) but also exacerbations of chronic obstructive pulmonary disease (COPD), chronic cough, complications of and/or primary cause of cystic fibrosis (CF) and community acquired pneumonia (CAP).

Infections might also occur in the oral cavity (caries, periodontitis) and caused by *Streptococcus mutans, Porphyromonas gingivalis, Aggregatibacter actinomycetemcomitans*. Infections might also be localized to the skin (abscesses, 'staph' infections, impetigo, secondary infection of burns, Lyme disease) and caused by *Staphylococcus aureus, Staphylococcus epidermidis, Pseudomonas aeruginosa* and *Borrelia burdorferi*. Infections of the urinary tract (UTI) can also be treated and are typically caused by *Escherichia coli*. Infections of the gastrointestinal tract (GI) (diarrhea, cholera, gall stones, gastric ulcers) are typically caused by *Salmonella enterica serovar, Vibrio cholerae* and *Helicobacter pylori*. Infections of the genital tract include and are typically caused by *Neisseria gonorrhoeae*. Infections can be of the bladder or of an indwelling device caused by *Enterococcus faecalis*. Infections associated with implanted prosthetic devices, such as artificial hip or knee replacements or dental implants or medical devices such as pumps or monitoring systems, typically caused by a variety of bacteria, can be treated by the methods of this invention. These devices can be coated or conjugated to an agent as described herein.

Infections caused by *Streptococcus agalactiae* are the major cause of bacterial septicemia in newborns. Such infections can also be treated by the methods of this invention. Likewise, infections caused by *Neisseria meningitidis* which can cause meningitis can also be treated.

Thus, routes of administration applicable to the methods of the invention include intranasal, intramuscular, intratracheal, subcutaneous, intradermal, topical application, intravenous, rectal, nasal, oral and other enteral and parenteral routes of administration. Routes of administration may be combined, if desired, or adjusted depending upon the agent and/or the desired effect. An active agent can be administered in a single dose or in multiple doses. Embodiments of these methods and routes suitable for delivery, include systemic or localized routes. In general, routes of administration suitable for the methods of the invention include, but are not limited to, enteral, parenteral or inhalational routes.

Parenteral routes of administration other than inhalation administration include, but are not limited to, topical, transdermal, subcutaneous, intramuscular, intraorbital, intracapsular, intraspinal, intrasternal and intravenous routes, i.e., any route of administration other than through the alimentary canal. Parenteral administration can be conducted to effect systemic or local delivery of the inhibiting agent. Where systemic delivery is desired, administration typically involves invasive or systemically absorbed topical or mucosal administration of pharmaceutical preparations.

The compounds of the invention can also be delivered to the subject by enteral administration. Enteral routes of administration include, but are not limited to, oral and rectal (e.g., using a suppository) delivery.

Methods of administration of the active through the skin or mucosa include, but are not limited to, topical application of a suitable pharmaceutical preparation, transcutaneous transmission, transdermal transmission, injection and epidermal administration. For transdermal transmission, absorption promoters or iontophoresis are suitable methods. Iontophoretic transmission may be accomplished using commercially available "patches" that deliver their product continuously via electric pulses through unbroken skin for periods of several days or more.

In various embodiments of the methods of the invention, the active will be administered orally on a continuous, daily basis, at least once per day (QD) and in various embodiments two (BID), three (TID) or even four times a day. Typically, the therapeutically effective daily dose will be at least about 1 mg, or at least about 10 mg, or at least about 100 mg or about 200-about 500 mg and sometimes, depending on the compound, up to as much as about 1 g to about 2.5 g.

Dosing of can be accomplished in accordance with the methods of the invention using capsules, tablets, oral suspension, suspension for intra-muscular injection, suspension for intravenous infusion, gel or cream for topical application or suspension for intra-articular injection.

Dosage, toxicity and therapeutic efficacy of compositions described herein can be determined by standard pharmaceutical procedures in cell cultures or experimental animals, for example, to determine the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compositions which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the methods, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In some embodiments, an effective amount of a composition sufficient for achieving a therapeutic or prophylactic effect, ranges from about 0.000001 mg per kilogram body weight per administration to about 10,000 mg per kilogram body weight per administration. Suitably, the dosage ranges are from about 0.0001 mg per kilogram body weight per administration to about 100 mg per kilogram body weight per administration. Administration can be provided as an initial dose, followed by one or more "booster" doses.

Booster doses can be provided a day, two days, three days, a week, two weeks, three weeks, one, two, three, six or twelve months after an initial dose. In some embodiments, a booster dose is administered after an evaluation of the subject's response to prior administrations.

The skilled artisan will appreciate that certain factors may influence the dosage and timing required to effectively treat a subject, including but not limited to, the severity of the disease or disorder, previous treatments, the general health and/or age of the subject, and other diseases present. Moreover, treatment of a subject with a therapeutically effective amount of the therapeutic compositions described herein can include a single treatment or a series of treatments.

Combination Therapy

The compositions and related methods of the present invention may be used in combination with the administration of other therapies. These include, but are not limited to, the administration of DNase enzymes, antibiotics, antimicrobials, or other antibodies.

In some embodiments, the methods and compositions include a deoxyribonuclease (DNase) enzyme that acts synergistically with a composition of this disclosure, e.g., a DNase. A DNase is any enzyme that catalyzes the cleavage of phosphodiester linkages in the DNA backbone. Three non-limiting examples of DNase enzymes that are known to target not only cruciform structures, but also a variety of secondary structure of DNA include DNAse I, T4 EndoVII and T7 Endo I. In certain embodiments, the effective amount of anti-DNABII antibody needed to destabilize the biofilm is reduced when combined with a DNase. When administered in vitro, the DNase can be added directly to the assay or in a suitable buffer known to stabilize the enzyme. The effective unit dose of DNase and the assay conditions may vary, and can be optimized according to procedures known in the art.

In other embodiments, the methods and compositions can be combined with antibiotics and/or antimicrobials. Antimicrobials are substances that kill or inhibit the growth of microorganisms such as bacteria, fungi, or protozoans. Although biofilms are generally resistant to the actions of antibiotics, compositions and methods described herein can be used to sensitize the infection involving a biofilm to traditional therapeutic methods for treating infections. In other embodiments, the use of antibiotics or antimicrobials in combination with methods and compositions described herein allow for the reduction of the effective amount of the antimicrobial and/or biofilm reducing agent. Some non-limiting examples of antimicrobials and antibiotics useful in combination with methods of the current invention include amoxicillin, amoxicillin-clavulanate, cefdinir, azithromycin, and sulfamethoxazole-trimethoprim. The therapeutically effective dose of the antimicrobial and/or antibiotic in combination with the biofilm reducing agent can be readily determined by traditional methods. In some embodiments the dose of the antimicrobial agent in combination with the biofilm reducing agent is the average effective dose which has been shown to be effective in other bacterial infections, for example, bacterial infections wherein the etiology of the infection does not include a biofilm. In other embodiments, the dose is 0.1, 0.15, 0.2, 0.25, 0.30, 0.35, 0.40, 0.45, 0.50, 0.55, 0.60, 0.65, 0.70, 0.75, 0.8, 0.85, 0.9, 0.95, 1.1, 1.2, 1.3, 1.4, 1.5, 1.6, 1.7, 1.8, 1.9, 2.0, 2.5, 3.0 or 5 times the average effective dose. The antibiotic or antimicrobial can be added prior to, concurrent with, or subsequent to the addition of the anti-DNABII antibody.

In other embodiments, the methods and compositions can be combined with antibodies that treat the bacterial infection. One example of an antibody useful in combination with the methods and compositions described herein is an antibody directed against an unrelated outer membrane protein (e.g., OMP P5). Treatment with this antibody alone does not debulk a biofilm in vitro. Combined therapy with this antibody and a biofilm reducing agent results in a greater effect than that which could be achieved by either reagent used alone at the same concentration. Other antibodies that may produce a synergistic effect when combined with a biofilm reducing agent or methods to reduce a biofilm include anti-rsPilA, anti-OMP26, anti-OMP P2, and anti-whole OMP preparations.

The compositions and methods described herein can be used to sensitize the bacterial infection involving a biofilm to common therapeutic modalities effective in treating bacterial infections without a biofilm but are otherwise ineffective in treating bacterial infections involving a biofilm. In other embodiments, the compositions and methods described herein can be used in combination with therapeutic modalities that are effective in treating bacterial infections involving a biofilm, but the combination of such additional therapy and biofilm reducing agent or method produces a synergistic effect such that the effective dose of either the biofilm reducing agent or the additional therapeutic agent can be reduced. In other instances the combination of such additional therapy and biofilm reducing agent or method produces a synergistic effect such that the treatment is enhanced. An enhancement of treatment can be evidenced by a shorter amount of time required to treat the infection.

The additional therapeutic treatment can be added prior to, concurrent with, or subsequent to methods or compositions used to reduce the biofilm, and can be contained within the same formulation or as a separate formulation.

Kits

Kits containing the agents and instructions necessary to perform the in vitro and in vivo methods as described herein also are claimed. Accordingly, the invention provides kits for performing these methods which may include a biological agent of this invention as well as instructions for carrying out the methods of this invention such as collecting tissue and/or performing the screen and/or analyzing the results and/or administration of an effective amount of biological agent as defined herein. These can be used alone or in combination with other suitable antimicrobial agents.

In one embodiment, the present disclosure provides a kit comprising a polypeptide comprising an HMG-box domain and instructions for use in breaking down a biofilm or inhibiting, preventing or treating a microbial infection that produces a biofilm. Examples of polypeptides comprising an HMG-box domain are described above. In one embodiment, the kit further comprises one or more of an adjuvant, an antigenic peptide or an antimicrobial. In yet another embodiment, the kit further comprises a carrier selected from the group of a liquid carrier, a pharmaceutically acceptable carrier, a solid phase carrier, a pharmaceutically acceptable carrier, an implant, a stent, a paste, a gel, a dental implant or a medical implant.

The following example is intended to illustrate, but not limit the invention.

EXPERIMENTAL

Example 1

Preparation of HMGB1 Antibodies

Methods and Materials for Western Blot

1. Ran 1 µg/well of following purified proteins on SDS—Page gels (Bio-Rad Mini PROTEAN™ TGX gels Catalogue #456-1093): IHF, HU, TBP and HMG1
2. Loaded 20 µl total to each well; ran at 125 V.
3. Transferred to nitrocellulose for 1 hour at 100V at 4° C.
4. Blocked nitrocellulose with 2% BSA in TTBS for 1 hour on rocking platform.
5. Incubated with primary antibody, for 1 hour on rocking platform in 1% BSA-TTBS primary antibodies used and dilution:
naïve rabbit serum (1:5000)
rabbit anti-IHF (1:10,000)
rabbit anti-TBP (1:10,000)
6. Washed 3 times with TTBS; 5 minutes each wash.
7. Incubated with secondary antibody for 1 hour on rocking platform in 1% BSA-TTBS. Secondary Antibody: Goat anti-rabbit IgG-HRP (1:10,000).
8. Washed 3 times with TTBS for 5 minutes per wash. Developed with CN/DAB.

Figure 2:
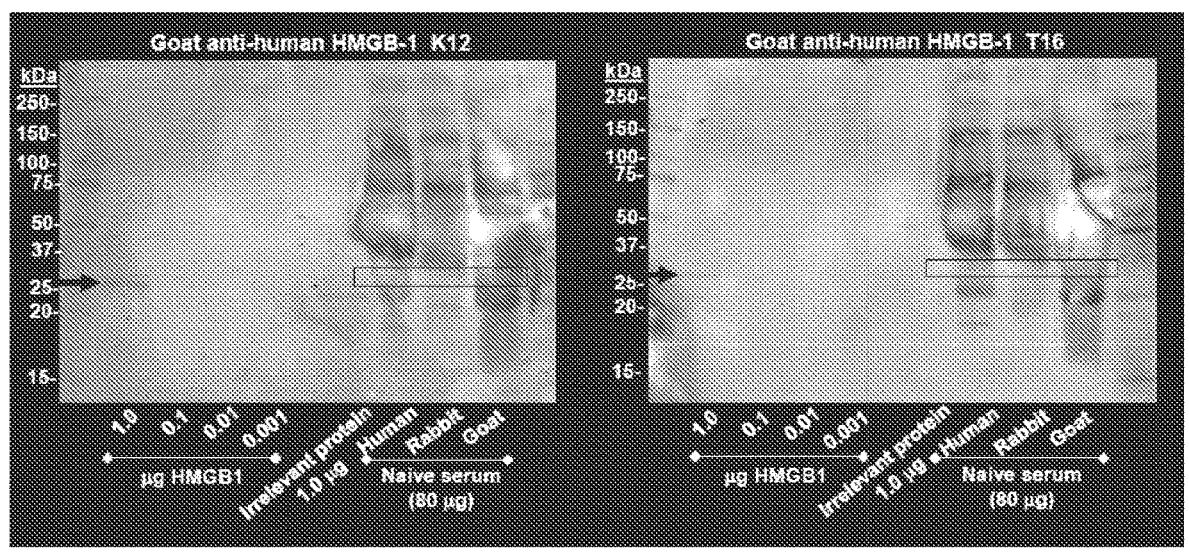
FIG. 2 are Western blot gel pictures showing the binding specificity of goat anti-human HMGB1 antibodies and that HMGB1 is found in naive serum.

As shown in FIG. 1, these antibodies are specific to the corresponding proteins. FIG. 2 further shows that the goat anti-human HMGB1 antibodies are specific to the human HMGB1 protein and the binding is in a dose-dependent manner.

Therefore, these antibodies are suitable for testing the binding of HMGB1 to DNA scaffold in microbial biofilms. Subsequent experiments shows that HMGB1 protein binds to DNA scaffold in microbial biofilms permitting immune response from the host leading to destruction and removal of the biofilm.

Example 2

HMGB1 Competes with HU and IHF for Binding to Biofilm DNA

This example demonstrates that HMGB1 has high affinity for bent DNA structures and competes with HU and IHF for binding to the DNA in biofilm leading to reduction of biofilm growth.

Figure 3:
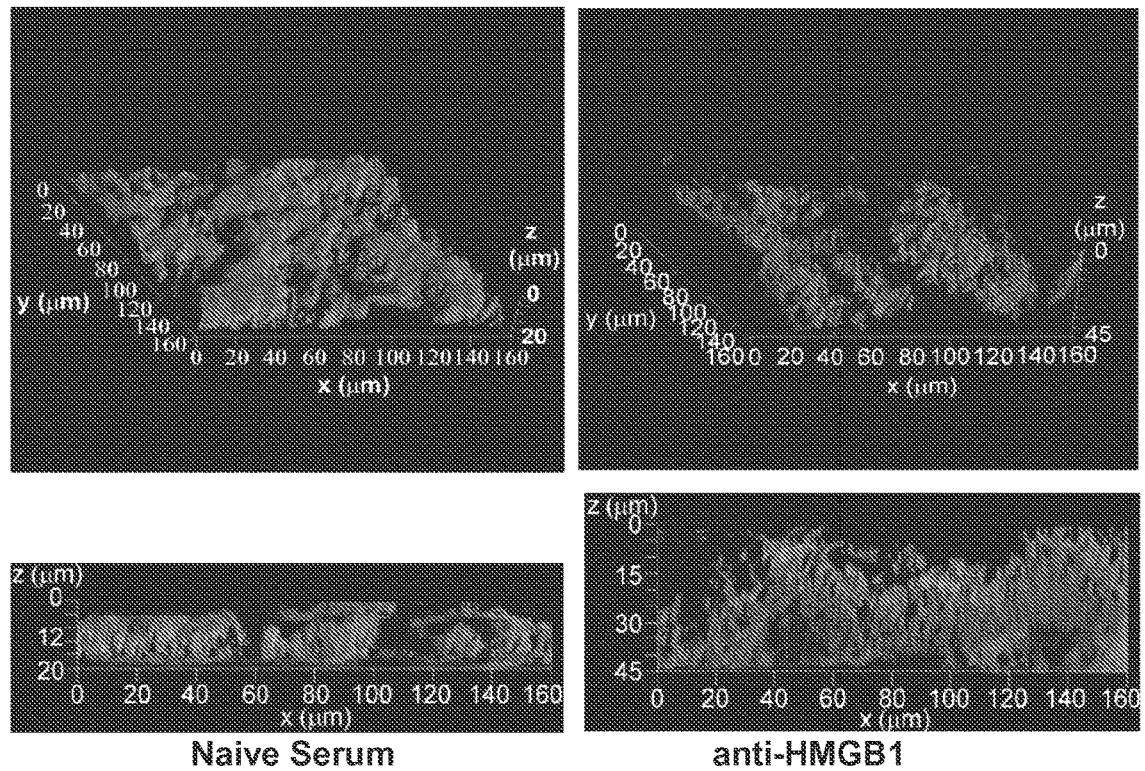
FIG. 3 presents confocal microscopy images of 40 h in vitro NTHI biofilms not treated (left) or treated (right) with anti-HMGB1 antibodies at 24 hours. The images show that reduction of HMGB1 found in naïve serum by the antibody caused enhanced biofilm growth, shown as thicker biofilm at lower right as compared to a thinner one at lower left.

To test the effect of HMGB1 on biofilms, biofilms generated by Nontypable *Haemophilus influenzae* (NTHI) were treated with naïve serum alone, which contained HMGB1, or with serum containing anti-HMGB1 antibody. As shown in FIG. 3, reduction of HMGB1 by the antibody caused enhanced biofilm growth, shown as thicker biofilm at lower right as compared to a thinner one at lower left. Therefore, less competition from HMGB1 for HU and IHF binding sites on the biofilm DNA strengthens the biofilm.

Figure 4:
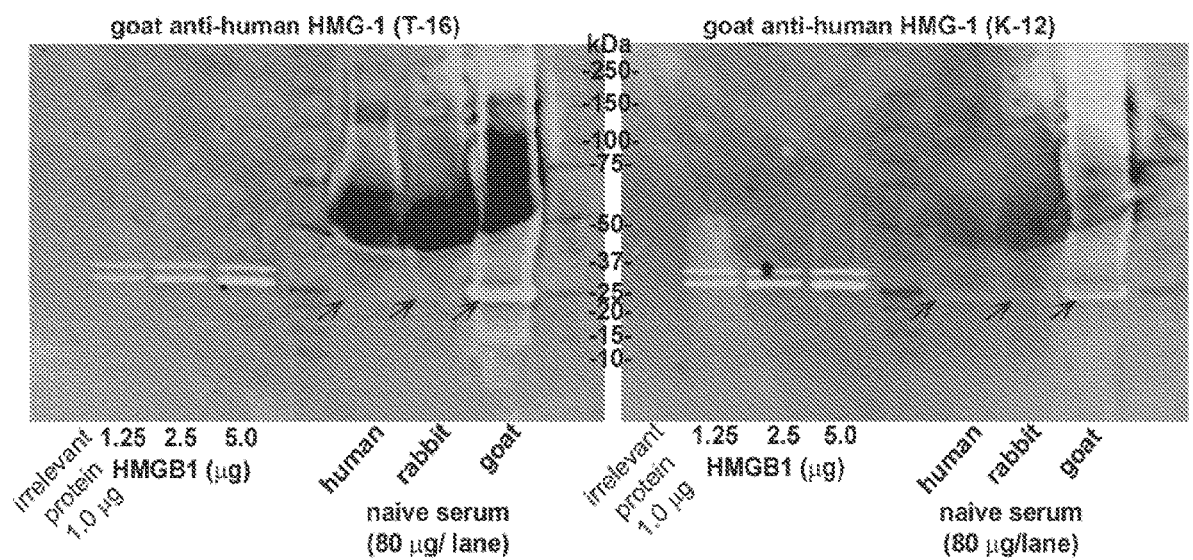
FIG. 4 includes gel images showing detection of HMGB1 in mammalian naïve serum by Western blot. The arrows indicate the detected HMGB1 in each sample. Note that HMGB1 had a His tag. Doublet observed in HMGB1 lanes was also present in example blot on specification sheet.

FIG. 4 confirms that HMGB1 protein exists in mammalian naïve serum and the HMGB1 protein from human, rabbit and goat can all be recognized by the prepared goat anti-human HMGB1 antibodies. The estimated concentrations of HMGB1 in each serum sample were about 0.8 µg, 0.8 µg, and 2.8 µg per 80 µg total protein, respectively.

Figure 5:
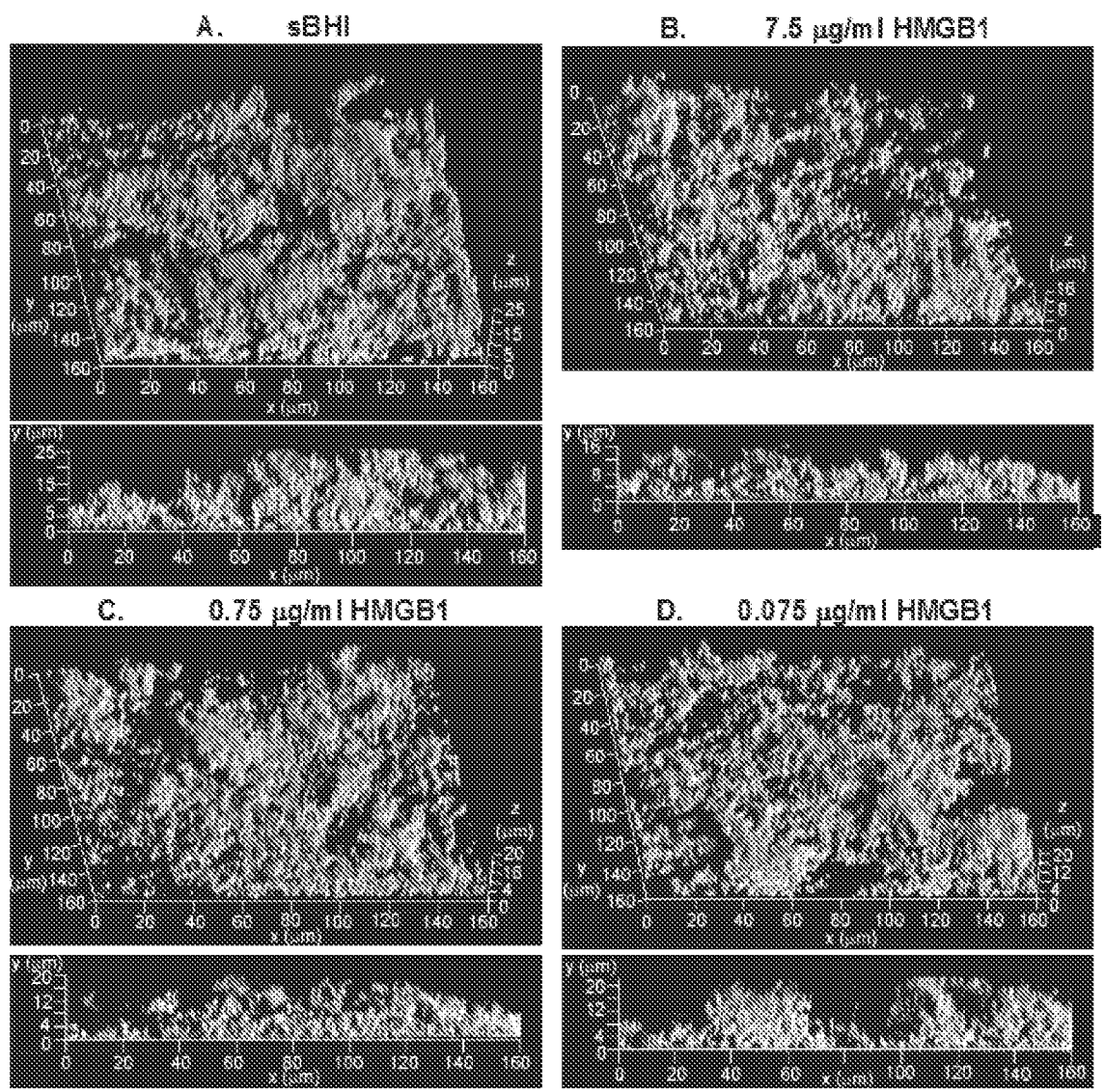
FIG. 5 presents confocal microscopy images of NTHI biofilms treated with different concentrations of HMGB1 and shows that HMGB1 dose-dependently inhibited biofilm formation. Control: in sterile medium sBHI (BHI with 2 mg heme/mL and 2 mg b-NAD/mL).

It was further discovered that HMGB1 dose-dependently inhibits biofilm formation. For instance, compared to NTHI in sterile medium sBHI (BHI with 2 mg heme/mL and 2 mg b-NAD/mL) that grew up to 22.5 µm of thickness at 40 hours, 0.075 µg/ml, 0.75 µg/ml and 7.5 µg/ml HMGB1 treatment at 24 hours reduced the biofilm thickness to 21.5 µm, 20.0 µm, and 16.5 µm, respectively (FIG. 5). This indicates that HMGB1 competes for the same binding target as HU and IHF.

Figure 6:
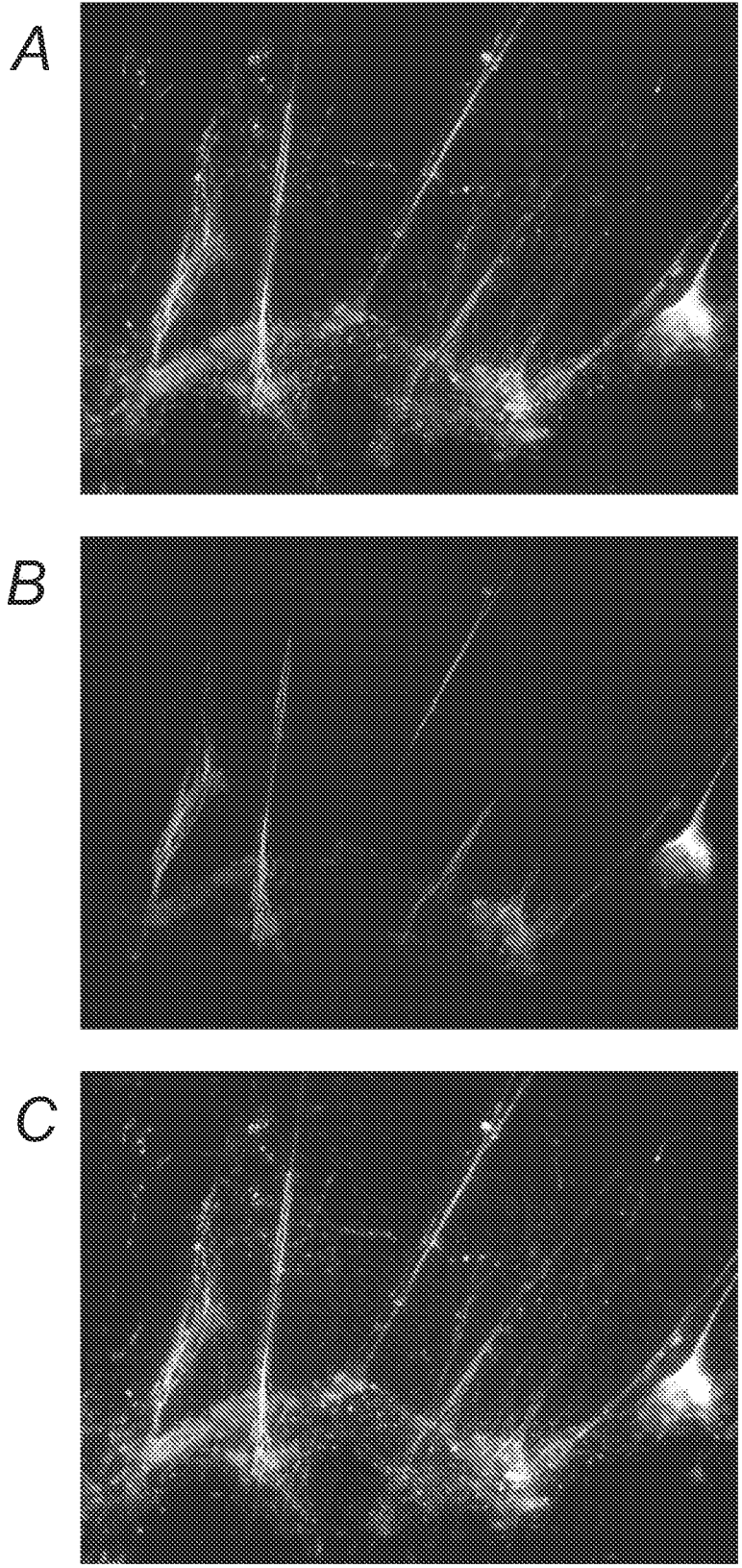
FIG. 6 presents dual labeling images of HMBG1 and IHF in bronchoalveolar lavage (BAL): A, labeling of HMGB1 with AlexaFluor 488 conjugated antibodies; B, labeling of IHF with AlexaFluor 594 conjugated antibodies; C, merged image of (A) and (B) showing localization of both antibodies. DAPI was psuedocolored white in all images.

The competitive binding between HMGB1 and IHF was further confirmed by dual labeling. As shown in FIG. 6, HMGB1 and IHF were co-localized in an OCT (Optimal Cutting Temperature medium, available commercially from Fisher Scientific Cat. No. 14-373-65) embedded human bronchoalveolar lavage (BAL). The localization of HMGB1 was detected with AlexaFluor 488 conjugated antibodies (FIG. 6A); the localization of IHF was detected with AlexaFluor 594 conjugated antibodies (FIG. 6B); and FIG. 6C, a merged image between FIGS. 6A and 6B, shows the co-localization.

Figure 7:
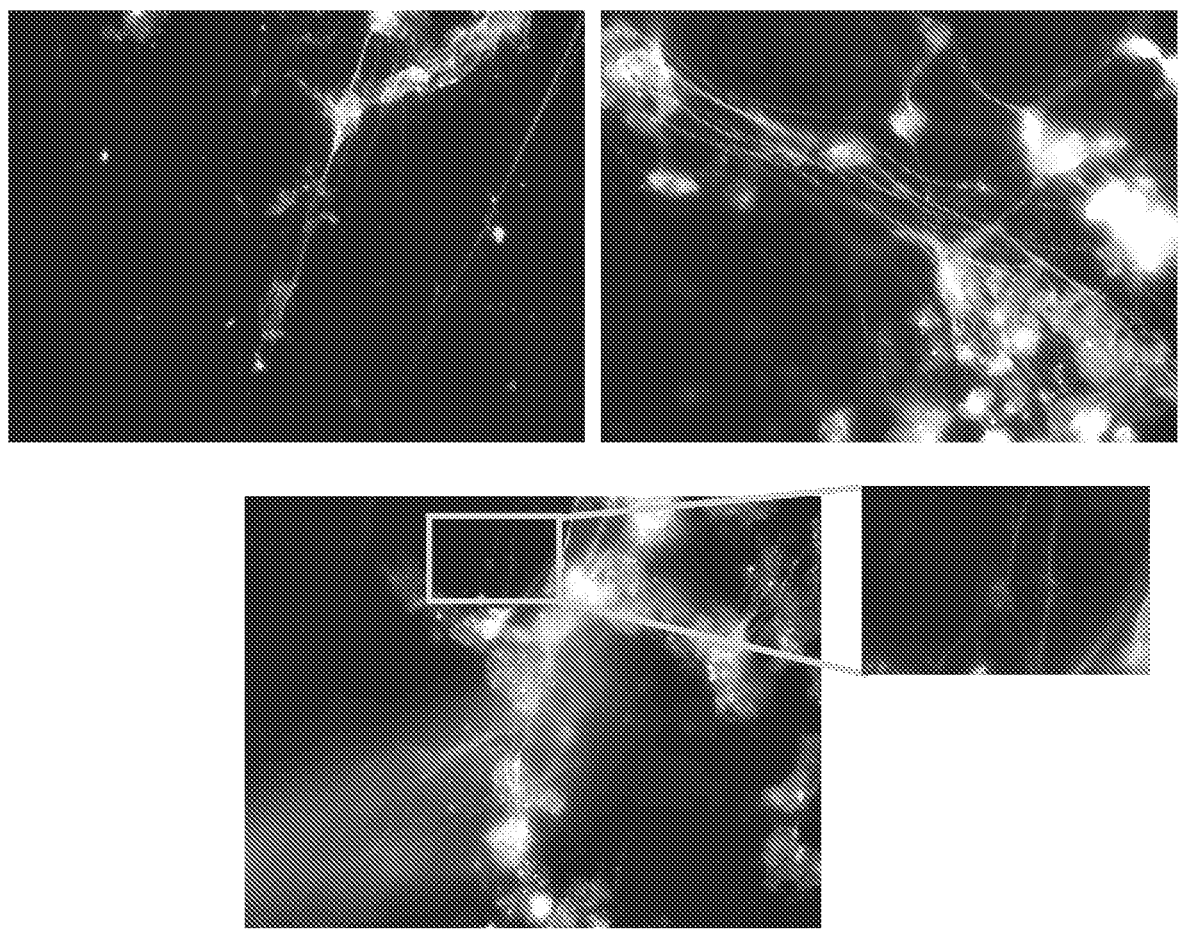
FIG. 7 presents microscopy images showing HMGB1 and IHF labeling of biomass formed by NTHI in the middle ear of a chinchilla. The images are from serial sections of an OCT embedded biomass co-labeled for HMGB1 and IHF using goat anti-HMGB1 (diluted 1:25) and rabbit anti-IHF (diluted 1:200). Labeling was detected using Donkey anti-Goat AlexaFluor 488 and Donkey anti-rabbit AlexaFluor 594. dsDNA was stained with DAPI and pseudocolored white.

Likewise, the co-localization of HMGB1 and IHF on biofilm was also observed in vivo on the NTHI biofilm formed in the middle year of a chinchilla (FIG. 7). Serial sections of an OCT embedded biomass were co-labeled for HMGB1 and IHF using goat anti-HMGB1 (diluted 1:25) and rabbit anti-IHF (diluted 1:200). Labeling was detected using Donkey anti-Goat AlexaFluor 488 and Donkey anti-rabbit AlexaFluor 594. dsDNA was stained with DAPI and pseudocolored white. In all images of FIG. 7, co-localization of HMGB1 and IHF on the biofilm DNA was observed.

Figure 8:
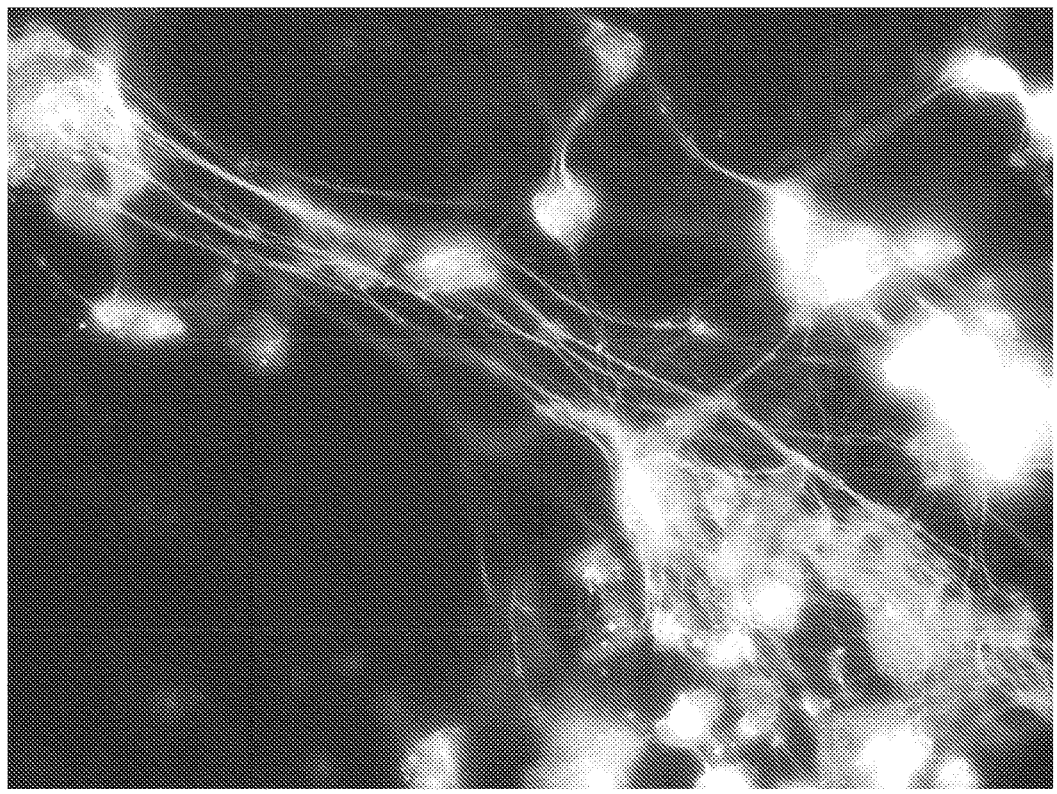
FIG. 8 shows that HMGB1 was detected periodically along the length of dsDNA strands. It was also found to be in close proximity of IHF at junctions.
Figure 9:
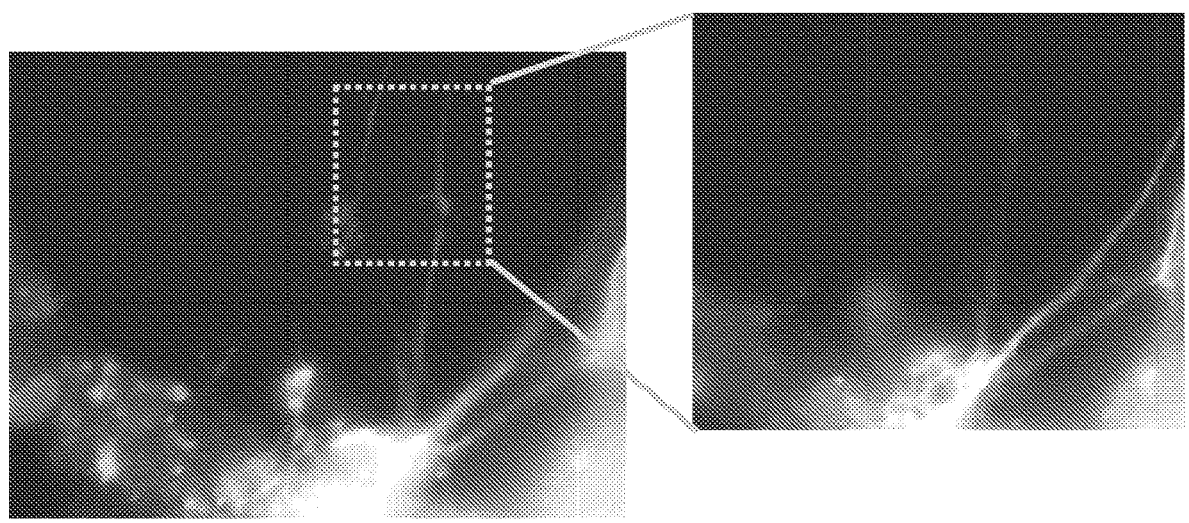
FIG. 9 presents different z-plane images of the same section of the slide. HMGB1 and IHF are both detected at the junction of strands of dsDNA and are in close proximity.

A further enlarged image in FIG. 8 shows that HMGB1 was periodically along the length of dsDNA strands and in close proximity of IHF at junctions. Moreover, different z-plane images of the same section of the slide (FIG. 9) show that HMGB1 and IHF are both detected at the junction of strands of dsDNA and are in close proximity.

Figure 10:
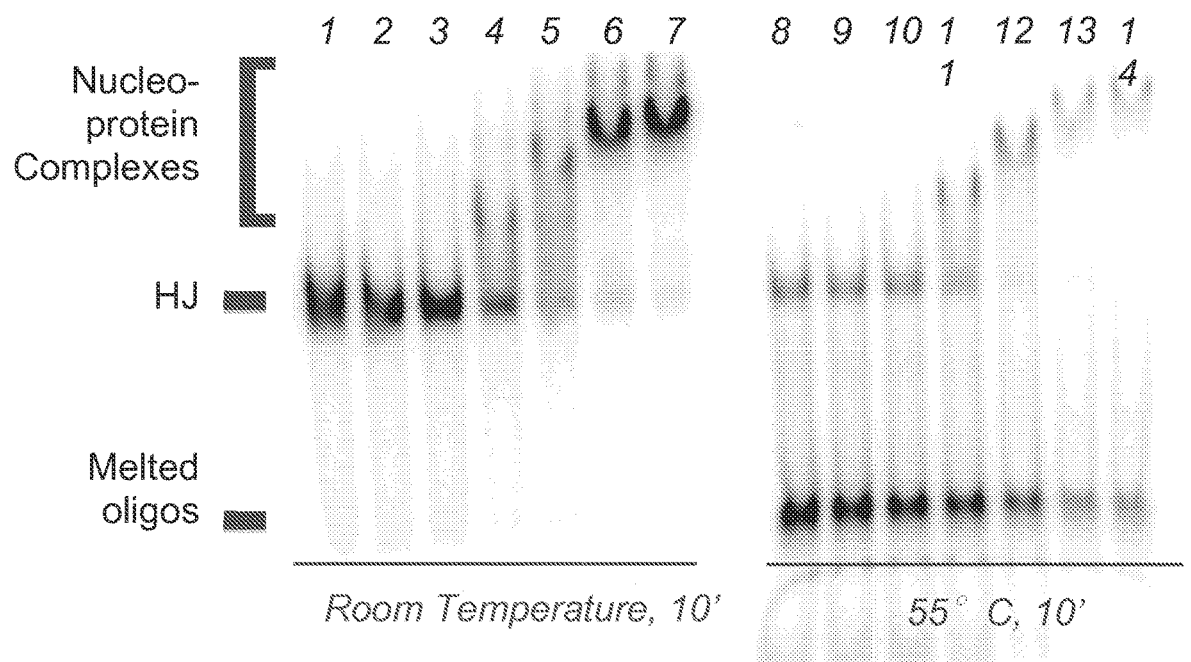
FIG. 10 presents an electromobility shift assay of HMGB1 bound to synthetic DNA Holliday junctions. Images show that HMGB1 failed to stabilize Holliday junction structural integrity with increasing temperature.

Different from IHF, however, electromobility shift assay of HMGB1 bound to synthetic DNA Holliday junctions show that HMGB1 fails to stabilize Holliday junction structural integrity with increasing temperature. (FIG. 10).

The data of this example therefore shows that HMGB1 competes with IHF and HU for binding to the same target on biofilm DNA. Exemplified by HMGB1, therefore, proteins containing a HMG-box domain is useful in inhibiting the formation and growth of biofilm and thus useful in treating diseases and conditions characterized by biofilms.

Example 3

This example described an animal model for the treatment of middle ear infections. Middle ear infection (or otitis media, OM) is a highly prevalent disease worldwide, afflicting 50-330 million children globally each year. The socioeconomic burden of OM is also great, with cost estimates between $5-6 billion in the United States alone annually. All three of the predominant bacterial pathogens of OM are known to form biofilms both in vitro and in vivo and recently, clinicians have come to appreciate that the chronicity and recurrence of OM is due, at least in part, to the formation of bacterial biofilms within the middle ear cavity. In one chinchilla model of OM, juvenile chinchillas are first given a viral 'cold', followed a week later by their being challenged intranasally with an inoculum of viable bacteria. Similar to the human condition wherein "my child has a cold and a week later gets an ear infection" chinchillas will also develop a bacterial OM approximately one week after a challenge, and while experiencing the viral upper respiratory tract infection. Once bacteria gain access to the middle ear (either via ascension of the Eustachian tube or following direct challenge to the middle ear space), they will form a robust biofilm. Applicants thus contemplate and indeed have already used chinchilla models to demonstrate the protective efficacy of the compositions and methods as described herein, which results in rapid resolution of existing biofilms. This model is also useful for therapeutic approaches via either passive delivery of anti-DNABII antibody or via delivery of a small molecule or other agent known to bind to IHF or other DNABII family members.

Example 4

A number of oral bacteria (e.g., *Aggregatibacter actinomycetemcomitans, Porphyromonas gingivalis*) have been implicated in the pathogenesis of inflammatory diseases such as periodontitis and peri-implantitis, which destroy alveolar bone and gingiva. Investigations of the pathogenesis of these bacteria are hampered by lack of effective animal models. One of the challenges of investigating the pathogenicity of specific bacteria is the difficulty of establishing a biofilm when exogenous bacteria are introduced into the oral cavity of animals. Though animal models of periodontitis have been developed, cultivable bacteria are rarely recovered from the oral cavity of inoculated animals. Developing an effective animal model which can assess the pathogenicity of specific bacteria will greatly aid in elucidating their pathogenic mechanisms.

The surface of machined titanium dental implants (1.2× 4.5 mm) can be modified by grit blasting with AlO3 (100 μm) and HCl etching (pH 7.8 for 20 min at 80° C.). Machined and nano-textured implants can be incubated in TSB medium inoculated with D7S clinical strain of *Aggregatibacter actinomycetemcomitans* (Aa) for 1 to 3 days at 37° C. The bacterial biofilm on the implants can be analyzed by SEM, as well as by confocal laser scanning microscopy following staining with LIVE/DEAD® BacLight™. Implants with and without established Aa biofilm are transmucosally placed into the alveolar bone of female rats between premolar and incisor region of the maxillae. To detect the presence of Aa biofilm on the implants placed in vivo, bacterial samples are collected from saliva and the oral surfaces of implants after 2 days. Aa was detected by culture, as well as by PCR analysis.

Example 5

This experiment provides a mouse model for pre-clinical testing of interfering agents to treat Lyme disease. See Dresser et al. Pathogens 5(12)e1000680, Epub 2009 Dec. 4. Lyme disease is the most common tick-borne disease in the United States. Reported cases have more than doubled between 1992 and 2006, with approximately 29,000 new cases confirmed in 2008. Estimates are that the actual number of cases of Lyme disease may exceed that reported by a factor of 6-12 in endemic areas. By definition, these endemic areas are expanding as populations continue to move from cities to suburban and rural areas and whitetail deer (which carry the tick species *Ixodes*) increasingly roam these areas. Lyme disease is caused by the microorganism *Borrelia burgdorferi*, a spirochete. *B. burgdorferi* is transmitted via the bite of the *Ixodes* tick and subsequently disseminates, via the bloodstream, to other tissues and organs.

In this animal model, C3H/HeN mice are injected with spirochetes via dorsal subcutaneous and intraperitoneal injection, or via intravenous injection. Blood and biopsy specimens are recovered at approximately 7 days post infection for evaluation of microbial burden and assessment of pathology in tissues and organs. The methods and compositions of this invention are contemplated to develop both therapeutic as well as preventative strategies for reduction and/or elimination of the resulting *B. burgdorferi* biofilms which form subsequent to challenge and are believed to contribute to both the pathogenesis and chronic nature of the disease.

Example 6

This experiment provides a porcine model for pre-clinical testing of agents to treat cystic fibrosis. See Stoltz et al. (2010) Science Translational Medicine 2(29): 29ra31. Cystic fibrosis is an autosomal recessive disease due to mutations in a gene that encodes the CF transmembrane conductance regulator (called CFTR) anion channel. In this model, pigs which have been specifically bred to carry a defect in the genes called "CFTR" and called CF pigs spontaneously develop hallmark features of CF lung disease that includes infection of the lower airway by multiple bacterial species. The pigs can be immunized with the interfering agents to either 1) immunize these CF pigs with a polypeptide or other immunogenic agent thereby inducing the formation of antibodies which will eradicate bacterial biofilms in the lungs, to deliver anti-IHF (or other interfering agent) to the lungs of these animals by nebulization to assess the amelioration of the signs of disease and associated pathologies.

Example 7

Applicants also provide a pre-clinical model for tuberculosis (TB). See Ordway et al. (2010) Anti. Agents and Chemotherapy 54:1820. The microorganism *Mycobacterium tuberculosis* is responsible for a growing global epidemic. Current figures suggest that there are approximately 8 million new cases of TB and about 2.7 million deaths due to TB annually. In addition to the role of this microbe as a co-infection of individuals with HIV (of the ~45 million infected with HIV, estimates are that ~⅓ are also co-infected with *M. tuberculosis*), its particularly troublesome that isolates have become highly resistant to multiple drugs and no new drug for TB has been introduced in over a quarter of a century. In this animal model, SPF guinea pigs are maintained in a barrier colony and infected via aerosolized spray to deliver ~20 cfu of *M. tuberculosis* strain Erdman K01 bacilli into their lungs. Animals are sacrificed with determination of bacterial load and recovery of tissues for histopathological assessment on days 25, 50, 75, 100, 125 and 150 days post-challenge. Unlike mice which do not develop classic signs of TB, guinea pigs challenged in this manner develop well-organized granulomas with central necrosis, a hallmark of human disease. Further, like humans, guinea pigs develop severe pyogranulomatous and necrotizing lymphadenitis of the draining lymph nodes as part of the primary lesion complex. Use of this model will provide a pre-clinical screen to confirm and identify therapeutic as well as preventative strategies for reduction and/or elimination of the resulting *M. tuberculosis* biofilms which have been observed to form in the lungs of these animals subsequent to challenge and are believed to contribute to both the pathogenesis and chronicity of the disease.

Example 8

Multiple animal models of catheter/indwelling device biofilm infections are known. See Otto (2009) Nature Reviews Microbiology, 7:555. While typically considered normal skin flora, the microbe *Staphylococcus epidermidis* has become what many regard as a key opportunistic pathogen, ranking first among causative agents of nosocomial infections. Primarily, this bacterium is responsible for the majority of infections that develop on indwelling medical devices which are contaminated by this common skin colonizer during device insertion. While not typically life-threatening, the difficulty associated with treatment of these biofilm infections, combined with their frequency, makes them a serious public health burden. Current costs associated with treatment of vascular catheter associated bloodstream infections alone that are due to S. epidermidis amount to $2 billion annually in the United States. In addition to S. epidermidis, E. faecalis and S. aureus are also contaminations found on indwelling medical devices. There are several animal models of catheter-associated S. epidermidis infections including rabbits, mice, guinea pigs and rats all of which are used to study the molecular mechanisms of pathogenesis and which lend themselves to studies of prevention and/or therapeutics. Rat jugular vein catheters have been used to evaluate therapies that interfere with E. faecalis, S. aureus and S. epidermidis biofilm formation. Biofilm reduction is often measured three ways—(i) sonicate catheter and calculate CFUs, (ii) cut slices of catheter or simply lay on a plate and score, or (iii) the biofilm can be stained with crystal violet or another dye, eluted, and OD measured as a proxy for CFUs.

Example 9

Methods described herein may be used to elicit immune responses in humans and animals. Immunogenic compositions may be administered to a human and animal subjects in the presence of adjuvants such as but not limited to aluminum salts and liposomes. Those skilled in the art will understand that any number of pharmaceutically acceptable adjuvants can also be used. Immunogenic compositions may be administered to a human or animal subjects intramuscularly, subdermally, intranasally, or through any other suitable route. Immunogenic compositions may be prepared in a manner consistent with the selected mode of administration. Immunogenic compositions may take the form of polypeptides, nucleic acids, or a combination thereof, and may comprise full-length or partial antigens. Additionally or alternatively, immunogenic compositions may take the form of APCs pulsed with a particular antigen, or APCs transfected with one or more polynucleotides encoding a particular antigen. Administration may comprise a single dose of an immunogenic composition, or an initial administration, followed by one or more booster doses. Booster doses may be provided a day, two days, three days, a week, two weeks, three weeks, one, two, three, six or twelve months, or at any other time point after an initial dose. A booster dose may be administered after an evaluation of the subject's antibody titer.

Example 10

Methods described herein may be used to confer passive immunity on a non-immune subject. Passive immunity against a given antigen may be conferred through the transfer of antibodies or antigen binding fragments that specifically recognize or bind to a particular antigen. Antibody donors and recipients may be human or non-human subjects. Additionally or alternatively, the antibody composition may comprise an isolated or recombinant polynucleotide encoding an antibody or antigen binding fragment that specifically recognizes or binds to a particular antigen.

Passive immunity may be conferred in cases where the administration of immunogenic compositions poses a risk for the recipient subject, the recipient subject is immunocompromised, or the recipient subject requires immediate immunity. Immunogenic compositions may be prepared in a manner consistent with the selected mode of administration. Compositions may comprise whole antibodies, antigen binding fragments, polyclonal antibodies, monoclonal antibodies, antibodies generated in vivo, antibodies generated in vitro, purified or partially purified antibodies, or whole serum. Administration may comprise a single dose of an antibody composition, or an initial administration followed by one or more booster doses. Booster doses may be provided a day, two days, three days, a week, two weeks, three weeks, one, two, three, six or twelve months, or at any other time point after an initial dose. A booster dose may be administered after an evaluation of the subject's antibody titer.

It is to be understood that while the invention has been described in conjunction with the above embodiments, that the foregoing description and examples are intended to illustrate and not limit the scope of the invention. Other aspects, advantages and modifications within the scope of the invention will be apparent to those skilled in the art to which the invention pertains.

Unless otherwise defined, all technical and scientific terms used herein have the same meaning as commonly understood by one of ordinary skill in the art to which this invention belongs. All nucleotide sequences provided herein are presented in the 5' to 3' direction.

The inventions illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

It is to be understood that while the invention has been described in conjunction with the above embodiments, that the foregoing description and examples are intended to illustrate and not limit the scope of the invention. Other aspects, advantages and modifications within the scope of the invention will be apparent to those skilled in the art to which the invention pertains.

What is claimed is:

1. A method for inhibiting or preventing the binding of a deoxyribonucleic acid B II (DNABII) polypeptide to a microbial DNA in a biofilm present on the surface ex vivo, comprising contacting the microbial DNA in the biofilm with an amount of an isolated or recombinant polypeptide, the amount effective to inhibit or prevent the biofilm, the polypeptide comprising a high mobility group-box domain (HMG-box domain), thereby inhibiting or preventing the binding of the DNABII polypeptide to the microbial DNA.

2. The method of claim 1, wherein the isolated or recombinant polypeptide comprising the HMG-box domain comprises one or more of:
 (a) an isolated or recombinant polypeptide high mobility group box 1 (HMGB1) comprising from about amino acid 6 to about amino acid 76 or from about amino acid 90 to about amino acid 138 of SEQ ID NO: 1 or a polypeptide having at least 98% sequence identity to each thereof;
 (b) an isolated or recombinant polypeptide high mobility group box 2 (HMGB2) comprising from about amino acid 9 to about amino acid 76 or from about amino acid 95 to about amino acid 160 of SEQ ID NO: 2 or a polypeptide having at least 98% sequence identity to each thereof;
 (c) an isolated or recombinant polypeptide high mobility group box 3 (HMGB3) comprising from about amino acid 9 to about amino acid 75 or from about amino acid 98 to about amino acid 158 of SEQ ID NO: 3 or a polypeptide having at least 98% sequence identity to each thereof; or
 (d) an isolated or recombinant polypeptide high mobility group box 4 (HMGB 4) comprising from about amino acid 9 to about amino acid 75 or from about amino acid 93 to about amino acid 158 of SEQ ID NO: 4 or a polypeptide having at least 98% sequence identity to each thereof.

3. The method of claim 2, wherein the isolated or recombinant polypeptide comprising an HMG-box (high mobility group-box) domain comprises one or more of:
 (a) a polypeptide having at least 99% sequence identity to a polypeptide from about amino acid 6 to about amino acid 76 or from about amino acid 90 to about amino acid 138 of SEQ ID NO: 1;
 (b) a polypeptide having at least 99% sequence identity to comprising a polypeptide from about amino acid 9 to about amino acid 76 or from about amino acid 95 to about amino acid 160 SEQ ID NO: 2;
 (c) a polypeptide having at least 99% sequence identity to comprising a polypeptide from about amino acid 9 to about amino acid 75 or from about amino acid 98 to about amino acid 158 SEQ ID NO: 3; or
 (d) a polypeptide having at least 99% sequence identity to comprising a polypeptide from about amino acid 9 to about amino acid 75 or from about amino acid 93 to about amino acid 158 of SEQ ID NO: 4.

4. The method of claim 2, wherein the isolated or recombinant polypeptide is a mammalian polypeptide that is or is not post-translationally modified, a mammalian polypeptide that is or is not post-translationally alkylated, and a polypeptide expressed in a non-mammalian system.

5. The method of claim 4, wherein the mammalian polypeptide is a human polypeptide.

6. The method of claim 1, wherein the isolated or recombinant polypeptide comprising an HMG-box (high mobility group-box) domain comprises one or more of:
 (a) a polypeptide comprising from about amino acid 6 to about amino acid 76 or from about amino acid 90 to about amino acid 138 of SEQ ID NO: 1;
 (b) a polypeptide comprising from about amino acid 9 to about amino acid 76 or from about amino acid 95 to about amino acid 160 SEQ ID NO: 2;
 (c) a polypeptide comprising nucleotides from about amino acid 9 to about amino acid 75 or from about amino acid 98 to about amino acid 158 SEQ ID NO: 3; or
 (d) a polypeptide comprising nucleotides from about amino acid 9 to about amino acid 75 or from about amino acid 93 to about amino acid 158 of SEQ ID NO: 4.

7. The method of claim 1, wherein the isolated or recombinant polypeptide comprising the HMG-box domain comprises one or more of:
 (a) an isolated or recombinant polypeptide high mobility group box 1 (HMGB1) consisting of from about amino acid 6 to about amino acid 76 of SEQ ID NO: 1 or a polypeptide having at least 98% sequence identity thereto;
 (b) an isolated or recombinant polypeptide high mobility group box 2 (HMGB2) consisting of from about amino acid 9 to about amino acid 76 of SEQ ID NO: 2 or a polypeptide having at least 98% sequence identity thereto;
 (c) an isolated or recombinant polypeptide high mobility group box 3 (HMGB3) consisting of from about amino acid 9 to about amino acid 75 of SEQ ID NO: 3 or a polypeptide having at least 98% sequence identity thereto; or
 (d) an isolated or recombinant polypeptide high mobility group box 4 (HMGB 4) consisting of from about amino acid 9 to about amino acid 75 of SEQ ID NO: 4 or a polypeptide having at least 98% sequence identity thereto.

8. The method of claim 7, wherein the isolated or recombinant polypeptide is a mammalian polypeptide that is or is not post-translationally modified, a mammalian polypeptide that is or is not post-translationally alkylated, and a polypeptide expressed in a non-mammalian system.

9. The method of claim 8, wherein the mammalian polypeptide is a human polypeptide.

* * * * *

UNITED STATES PATENT AND TRADEMARK OFFICE
CERTIFICATE OF CORRECTION

PATENT NO. : 10,595,530 B2
APPLICATION NO. : 14/885800
DATED : March 24, 2020
INVENTOR(S) : Steven D. Goodman and Lauren O. Bakaletz It is certified that error appears in the above-identified patent and that said Letters Patent is hereby corrected as shown below:

In the Specification

Column 1, following after the "Cross Reference to Related Applications" sub-heading and paragraph, and before the "Sequence Listing" sub-heading, add new sub-heading and paragraph:

STATEMENT OF GOVERNMENT SUPPORT
"This invention was made with government support under R01 DE013230 awarded by the National Institutes of Health. The government has certain rights in the invention."

Signed and Sealed this
Third Day of December, 2024

Katherine Kelly Vidal
*Director of the United States Patent and Trademark Office*